US007462322B2

(12) United States Patent
Leland et al.

(10) Patent No.: US 7,462,322 B2
(45) Date of Patent: *Dec. 9, 2008

(54) METHODS AND APPARATUS FOR IMPROVED LUMINESCENCE ASSAYS

(75) Inventors: John K. Leland, Laurel, MD (US); Haresh P. Shah, Gaithersburg, MD (US); John H. Kenten, Gaithersburg, MD (US); Jack E. Goodman, Arlington, VA (US); George E. Lowke, Laytonsville, MD (US); Yuzaburo Namba, Ibaraki (JP); Gary F. Blackburn, Gaithersburg, MD (US); Richard J. Massey, Rockville, MD (US)

(73) Assignee: Bioveris Corporation, Gaithersburg, MD (US)

( * ) Notice: Subject to any disclaimer, the term of this patent is extended or adjusted under 35 U.S.C. 154(b) by 508 days.

This patent is subject to a terminal disclaimer.

(21) Appl. No.: 10/912,574

(22) Filed: Aug. 6, 2004

(65) Prior Publication Data

US 2005/0164410 A1   Jul. 28, 2005

Related U.S. Application Data

(60) Division of application No. 08/465,443, filed on Jun. 5, 1995, now Pat. No. 6,881,589, which is a division of application No. 08/346,832, filed on Nov. 30, 1994, now Pat. No. 5,935,779, which is a continuation of application No. 08/158,193, filed on Nov. 24, 1993, now abandoned, which is a continuation of application No. 07/652,427, filed on Feb. 6, 1991, now abandoned.

(51) Int. Cl.
*G01N 21/76* (2006.01)
*G01N 33/553* (2006.01)
*G01N 27/26* (2006.01)
*C12M 1/00* (2006.01)

(52) U.S. Cl. .................. 422/52; 436/172; 436/526; 204/400; 204/403.1

(58) Field of Classification Search ............... 422/52; 436/172, 526; 204/400, 403.1
See application file for complete search history.

(56) References Cited

U.S. PATENT DOCUMENTS

| 5,466,416 | A | * | 11/1995 | Ghaed et al. | 422/52 |
| 5,624,637 | A | * | 4/1997 | Ghaed et al. | 422/52 |
| 5,700,427 | A | * | 12/1997 | Ghaed et al. | 422/52 |
| 5,720,922 | A | * | 2/1998 | Ghaed et al. | 422/52 |
| 5,744,367 | A | * | 4/1998 | Talley et al. | 436/172 |
| 5,746,974 | A | * | 5/1998 | Massey et al. | 422/52 |
| 5,779,976 | A | * | 7/1998 | Leland et al. | 422/52 |
| 5,798,083 | A | * | 8/1998 | Massey et al. | 422/52 |
| 6,133,043 | A | * | 10/2000 | Talley et al. | 436/172 |
| 6,325,973 | B1 | * | 12/2001 | Leland et al. | 422/52 |

* cited by examiner

*Primary Examiner*—Mark L. Shibuya
(74) *Attorney, Agent, or Firm*—Foley & Lardner LLP

(57) ABSTRACT

An apparatus for performing a binding assay for an analyte of interest present in a sample based upon measurement of electrochemiluminescence at an electrode surface comprising a cell defining a sample containing volume intersecting with inlet and outlet means, an electrode having a substantially horizontally positioned surface exposed to and positioned below a portion of the sample containing volume, means for impressing electrochemical energy upon said electrode sufficient to generate luminescence, means for magnetically collecting particles along said surface and means for measuring the luminescence generated at said electrode.

14 Claims, 23 Drawing Sheets

SEQUENCE LISTING

<160> NUMBER OF SEQ ID NOS: 18

<210> SEQ ID NO 1
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
ttagtgagta tagacattat tgttatagtt                                    30

<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 2
cagttaatac acctaattaa caaatcacac                                    30

<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
acaacattag aacagcaata caacaaaccg                                    30

<210> SEQ ID NO 4
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
ttagagaatt aagacattat tcagact                                       27

<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
caccgcaggc accttattaa taaattgtat                                    30

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
gacacattgg aaaaactaac taacactggg                                    30

<210> SEQ ID NO 7
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
gcgatgacgg aatataagct ggtggtggtg                                    30

<210> SEQ ID NO 8
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
```
ttctggatca gctggatggt cagcgcactc                               30

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
ggcgccgtcg gtgtgggcaa                                          20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
ggcgccggcg gtgtgggcaa                                          20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
ttgcccacac cgacggcgcc                                          20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
ttgcccacac cgccggcgcc                                          20

<210> SEQ ID NO 13
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
gtccaatcca tcttggcttg tcgaagtctg a                             31

<210> SEQ ID NO 14
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14

-continued

```
tcagacttcg acaacccaag atggattgga c                              31

<210> SEQ ID NO 15
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
tcagacttcg acaacccaag atggattgga                                30

<210> SEQ ID NO 16
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
gatttttcca ttgtggttga catcaaggaa                                30

<210> SEQ ID NO 17
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
gccacgcaag cgggtgagga gttcc                                     25

<210> SEQ ID NO 18
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
gtccgaggca aatgccaata atgg                                      24
```

METHODS AND APPARATUS FOR IMPROVED LUMINESCENCE ASSAYS

This is a divisional of application Ser. No. 08/465,443, filed Jun. 5, 1995, now U.S. Pat. No. 6,881,589 now allowed, which is a divisional of application Ser. No. 08/346,832, filed Nov. 30, 1994, now U.S. Pat. No. 5,935,779, which is a Continuation of application Ser. No. 08/158,193, filed Nov. 24, 1993, now abandoned, which is a Continuation of application Ser. No. 07/652,427, filed Feb. 6, 1991, now abandoned, all of which are incorporated herein by reference.

FIELD OF THE INVENTION

This application relates generally to methods and apparatus for conducting binding assays, more particularly to those which measure the presence of an analyte of interest by measuring luminescence emitted by one or more labeled components of the assay system. More specifically, the invention relates to precise, reproducible, accurate homogeneous or heterogeneous specific binding assays of improved sensitivity in which the luminescent component is concentrated in the assay composition and collected on the detection system before being caused to electrochemiluminescence.

BACKGROUND OF THE INVENTION

Numerous methods and systems have been developed for the detection and quantitation of analytes of interest in biochemical and biological substances. Methods and systems which are capable of measuring trace amounts of microorganisms, pharmaceuticals, hormones, viruses, antibodies, nucleic acids and other proteins are of great value to researchers and clinicians.

A very substantial body of art has been developed based upon the well known binding reactions, e.g., antigen-antibody reactions, nucleic acid hybridization techniques, and protein-ligand systems. The high degree of specificity in many biochemical and biological binding systems has led to many assay methods and systems of value in research and diagnostics. Typically, the existence of an analyte of interest is indicated by the presence or absence of an observable "label" attached to one or more of the binding materials. Of particular interest are labels which can be made to luminesce through photochemical, chemical, and electrochemical means.

"Photoluminescence" is the process whereby a material is induced to luminesce when it absorbs electromagnetic radiation. Fluorescence and phosphorescence are types of photoluminescence. "Chemiluminescent" processes entail the creation of luminescent species by chemical transfer of energy. "Electrochemiluminescence" entails creation of luminescent species electrochemically.

Chemiluminescent assay techniques where a sample containing an analyte of interest is mixed with a reactant labeled with a chemiluminescent label have been developed. The reactive mixture is incubated and some portion of the labeled reactant binds to the analyte. After incubation, the bound and unbound fractions of the mixture are separated and the concentration of the label in either or both fractions can be determined by chemiluminescent techniques. The level of chemiluminescence determined in one or both fractions indicates the amount of analyte of interest in the biological sample.

Electrochemiluminescent (ECL) assay techniques are an improvement on chemiluminescent techniques. They provide a sensitive and precise measurement of the presence and concentration of an analyte of interest. In such techniques, the incubated sample is exposed to a voltammetric working electrode in order to trigger luminescence. In the proper chemical environment, such electrochemiluminescence is triggered by a voltage impressed on the working electrode at a particular time and in a particular manner. The light produced by the label is measured and indicates the presence or quantity of the analyte. For a fuller description of such ECL techniques, reference is made to PCT published application US85/01253 (WO86/02734), PCT published application US87/00987, and PCT published application U.S. 88/03947. The disclosures of the aforesaid applications are incorporated by reference.

It is desirable to carry out electrochemiluminescent assays without the need for a separation step during the assay procedure and to maximize the signal modulation at different concentrations of analyte so that precise and sensitive measurements can be made. Among prior art methods for non-separation assays are those which employ microparticulate matter suspended in the assay sample to bind one or more of the binding components of the assay.

U.S. Pat. No. 4,305,925 relates to the detection and determination of clinically relevant proteins and peptides by means of nephelometric and turbidimetric methods. The methods disclosed involve binding the antigen or antibody to latex particles which perform the function of light scattering or adsorption.

U.S. Pat. No. 4,480,042 relates to techniques employing particle reagents consisting of shell-core particles. The shell contains functional groups to which compounds of biological interest can be covalently bonded, and the high refractive index of the core results in high sensitivity to light scattering measurements. The technique is based upon agglutination reactions which result from the reaction of bivalent antibodies with multivalent antigens of interest to produce aggregates which can be detected and/or measured in various ways.

U.S. Pat. No. 4,419,453 likewise relates to the use of colored latex agglutination test methods useful for detecting the presence of immunochemicals such as antibodies and immunogens.

Based upon this prior art, it would not have appeared possible to use microparticulate matter in assays wherein a luminescent phenomenon is measured. One would expect that the luminescence from free chemiluminescent or electrochemiluminescent moieties would be absorbed, scattered, or otherwise suffer interference from the microparticulate matter.

Contrary to that expectation, U.S. application Ser. No. 539,389 (PCT published application U.S. 89/04919) teaches sensitive, specific binding assay methods based on a luminescent phenomenon wherein inert microparticulate matter is specifically bound to one of the binding reactants of the assay system. The assays may be performed in a heterogeneous (one or more separation steps) assay format and may be used most advantageously in a homogeneous (nonseparation) assay format.

U.S. 89/04919 relates to a composition for an assay based upon a binding reaction for the measurement of luminescent phenomenon, which composition includes a plurality of suspended particles having a surface capable of binding to a component of the assay mixture. In another aspect, it is directed to a system for detecting or quantitating an analyte of interest in a sample, which system is capable of conducting the assay methods using the assay compositions of the inventions. The system includes means for inducing the label compound in the assay medium to luminesce, and means for measuring the luminescence to detect the presence of the analyte of interest in the sample.

It was found that the binding of that component of the assay system to which an electrochemiluminescent moiety has been linked, to suspended microparticulate matter, greatly modulates the intensity of the luminescent signal generated by the electrochemiluminescent moiety linked to that component, thereby providing a means of monitoring the specific binding reaction of the assay system. Even more surprisingly, the suspended particles were found to have little or no effect on the intensity of the luminescent signal generated by the electrochemiluminescent moiety linked to the component of the system which remains unbound to the suspended microparticulate matter.

Thus, U.S. 89/04919 is directed to methods for the detection of an analyte of interest in a sample, which method includes the steps of (1) forming a composition comprising (a) a sample suspected of containing an analyte of interest, (b) an assay-performance-substance selected from the group consisting of (i) analyte of interest or analog of the analyte of interest, (ii) a binding partner of the analyte of interest or its said analog, and (iii) a reactive component capable of binding with (i) or (ii), wherein one of said substances is linked to a label compound having a chemical moiety capable of being induced to luminesce, and (c) a plurality of suspended particles capable of specifically binding with the analyte and/or a substance defined in (b) (i), (ii), or (iii); (2) incubating the composition to form a complex which includes a particle and said label compound; (3) inducing the label compound to luminesce; and (4) measuring the luminescence emitted by the composition to detect the presence of the analyte of interest in the sample. Those same methods may be used to quantify the amount of analyte in a sample by comparing the luminescence of the assay composition to the luminescence of a composition containing a known amount of analyte.

Analogs of the analyte of interest, which may be natural or synthetic, are compounds which have binding properties comparable to the analyte, but include compounds of higher or lower binding capability as well. Binding partners suitable for use in the present invention are well-known. Examples are antibodies, enzymes, nucleic acids, lectins, cofactors and receptors. The reactive components capable of binding with the analyte or its analog and/or with a binding partner thereof may be a second antibody or a protein such as Protein A or Protein G or may be avidin or biotin or another component known in the art to enter into binding reactions.

Advantageously, the luminescence arises from electrochemiluminescence (ECL) induced by exposing the label compound, whether bound or unbound to specific binding partners, to a voltammetric working electrode. The ECL reactive mixture is controllably triggered to emit light by a voltage impressed on the working electrode at a particular time and in a particular manner to generate light. Although the emission of visible light is an advantageous feature the composition or system may emit other types of electromagnetic radiation, such as infrared or ultraviolet light, X-rays, microwaves, etc. Use of the terms "electrochemiluminescence," "electrochemiluminescent" "electrochemiluminescence" "luminescence," "luminescent," and "luminesce" includes the emission of light and other forms of electromagnetic radiation.

The methods taught in U.S. 89/04919 permit the detection and quantitation of extremely small quantities of analytes in a variety of assays performed in research and clinical settings. The demands of researchers and clinicians makes it imperative, however, to lower the detection limits of assays performed by these methods to increase the sensitivities of those assays and to increase the speed at which they can be performed.

Various methods are known in the art for increasing the signal from labeled species by concentrating them before subjecting them to a measurement step. In U.S. Pat. No. 4,652,333, for example, particles labeled with fluorescent, phosphorescent or atomic fluorescent labels are concentrated by microfiltration before a measurement step is performed.

It is also known in the art to concentrate labeled immunochemical species prior to a measurement step, by, e.g., drawing magnetically responsive labeled particles to the surface of a measurement vessel. In U.S. Pat. Nos. 4,731,337, 4,777,145, and 4,115,535, for example, such particles are drawn to the vessel wall and then are irradiated to excite a fluorophoric emission of light.

In U.S. Pat. No. 4,945,045, particles are concentrated on a magnetic electrode. An electrochemical reaction takes place at the electrode facilitated by a labeled chemical mediator. The immunochemical binding reaction alters the efficiency of the mediator resulting in a modulated signal when binding takes place.

These prior art methods are not relevant to the surface selective excitation processes of the invention. While not being bound by any particular mechanistic explanation of surface excitation, e.g., electrochemiluminescence, it is believed that the label on the solid-phase complex must be oxidized at the electrode. This requires that an electron move from the label to the electrode. It is believed that the electron makes this "jump" by a phenomenon known as tunneling in which the electron passes through space (a region where its potential energy is very high, e.g., the solution) without having to go "over" the potential energy barrier. It can tunnel through the energy barrier, and thus, move from one molecule to another or from one molecule to an electrode without additional energy input. However, this tunneling phenomenon can only operate for very short distances. The probability of the tunneling phenomenon falls off exponentially as the distance between the two species increases. The probability of the tunneling phenomenon occurring between two species is fairly high if the distance is less than 25 Angstroms (2.5 nm) but is fairly low if the distance is greater. The distance of 25 Å is a rule-of-thumb used by those skilled in the art but is not an absolute limitation.

Accordingly, only those ECL labels with 25 Å of the surface of the electrode can be expected to participate in the ECL process. The area of the particle which is within 25 Å of the surface of an electrode is typically extremely small.

Accordingly, one would not expect that ECL from a particle surface would be measurable to any significant degree. Moreover, the light which is produced by the ECL process must pass through the particle to get to the photomultiplier. Since the particles are essentially opaque (a concentrated suspension of them is black) one would not expect that, even if significant amounts of light could be produced by ECL, that the light could pass through the particle and be measured by the photomultiplier.

OBJECTS OF THE INVENTION

It is therefore a primary object of this invention to provide homogeneous (non-separation) and heterogeneous (separation) methods, reagents and apparatus, for the conduct of binding assays.

It is a further object of this invention to provide non-separation, specific bonding assays, reagents and apparatus, based upon the measurement of electrochemiluminescence emitted from an assay composition containing microparticulate matter.

It is a further and related object to provide such assays, reagents and apparatus having improved sensitivity, faster assay time, greater sensitivity, lower detection limits and greater precision than has heretofore been achieved.

DESCRIPTION OF THE INVENTION

Definition of Terms

The term "ECL moiety," "metal-containing ECL moiety" "label," "label compound," and "label substance," are used interchangeably. It is within the scope of the invention for the species termed "ECL moiety," "metal-containing ECL moiety," "organometallic," "metal chelate," "transition metal chelate" "rare earth metal chelate," "label compound," "label substance" and "label" to be linked to molecules such as an analyte or an analog thereof, a binding partner of the analyte or an analog thereof, and further binding partners of such aforementioned binding partner, or a reactive component capable of binding with the analyte, an analog thereof or a binding partner as mentioned above. The above-mentioned species can also be linked to a combination of one or more binding partners and/or one or more reactive components. Additionally, the aforementioned species can also be linked to an analyte or its analog bound to a binding partner, a reactive component, or a combination of one or more binding partners and/or one or more reactive components. It is also within the scope of the invention for a plurality of the aforementioned species to be bound directly, or through other molecules as discussed above, to an analyte or its analog. For purposes of brevity, these ligands are referred to as an assay-performance-substance.

The terms detection and quantitation are referred to as "measurement", it being understood that quantitation may require preparation of reference compositions and calibrations.

The terms collection and concentration of complex may be used interchangeably to describe the concentration of complex within the assay composition and the collection of complex at, e.g., an electrode surface.

BRIEF DESCRIPTION OF THE INVENTION

Figure 1:
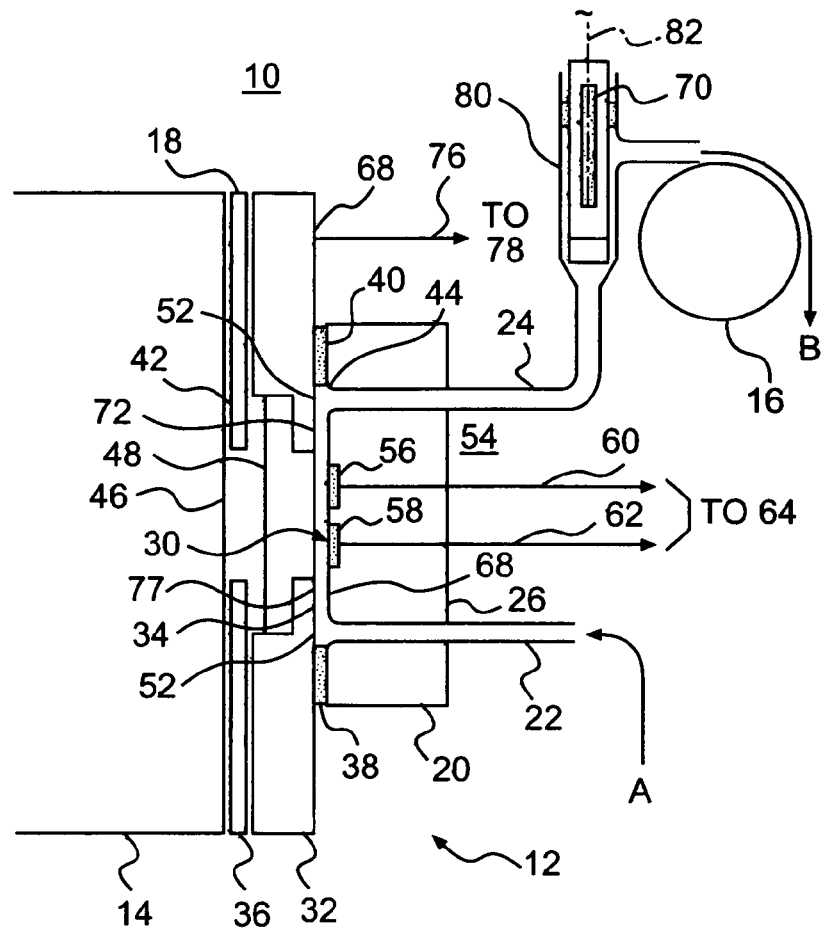
FIG. 1 is a schematic drawing of a cell for performing the microparticulate-based nonseparation and separation assays of the invention.

In its broadest embodiment, the invention is in a method for performing a binding assay for an analyte of interest present in a sample. The steps include:
(a) forming a composition containing
  (i) said sample
  (ii) an assay-performance-substance which contains a component linked to a label compound capable of being induced to luminesce, and
  (iii) a plurality of particles capable of specifically binding with the analyte and/or said assay-performance-substance;
(b) incubating said composition to form a complex which includes a particle and said label compound;
(c) collecting said complex in a measurement zone;
(d) inducing the label compound in said complex to luminesce by surface selective excitation; and
(e) measuring the emitted luminescence to measure the presence of the analyte of interest in the sample.

The complex may be collected on, e.g., an electrode surface where it is excited and induced to electrochemiluminesce, as by impressing a voltage on the electrode, or, it may be collected on a surface and be thereafter induced to fluoresce by surface excitation as described below. Total-internal-reflection-fluorescence (TIRF) has been described [cite reference] as a surface sensitive technique for exciting and detecting fluorophoric labels and total-internal-reflection has been used with RAMAN [cite reference] and infra-red absorption [cite reference] as another surface-sensitive technique for measuring the presence of a label. Surface plasmon resonance is an optical technique which may be used according to methods of the invention to measure labels on surfaces. The invention is thus directed to methods for exciting luminescence by surface excitation techniques.

While the invention is preferably carried out by collecting the complex in a measurement zone, i.e., on a surface at which it can be caused to luminesce, the invention also embraces methods wherein the complex is collected in a measurement zone and thereafter means are brought to that zone or other steps taken to induce and measure luminescence.

The collection of the complex may be carried out by several different methods, including gravity settling, filtration, centrifugation and magnetic attraction of magnetically responsive particles which form part of the complex. The several embodiments are described in further detail below.

Assays based upon the measurement of electrochemiluminescence at an electrode surface are advantageously carried out using the forces of gravity by
  (a) forming a composition containing
    (i) said sample
    (ii) an assay-performance-substance which contains a component linked to a label compound capable of being induced to electrochemiluminesce, and
    (iii) a plurality of suspended particles having a density greater than the balance of said composition and being capable of specifically binding with the analyte and or said assay-performance-substance;
  (b) incubating said composition to form a complex which includes a particle and said label compound;
  (c) introducing said composition into an assay cell;
  (d) collecting said complex at the surface of an electrode located below at least a substantial portion of the volume of said assay cell by permitting said composition to reside in said cell for a time sufficient to permit the particles to settle upon said electrode surface by the force of gravity;
  (e) inducing the label compound in said collected complex to luminescence by imposing a voltage on said electrode; and
  (f) measuring the emitted luminescence at the electrode surface to measure the presence of the analyte of interest in the sample.

While batch assays can be performed, continuous or semi-continuous assays can be performed in flow cells. In a flow cell, the solid-phase remains in the measurement cell while the solution flows through and exits the cell. If the solid-phase (e.g., particles) are more dense than water, i.e., have a density greater than that of water, (more than 1.0 g/mL) the force of gravity upon the particles causes them to fall to the bottom of the cell. The cell can be constructed such that the particles settle to the bottom as the fluid flows through the cell or the cell can be constructed such that the majority of the sample is contained in the cell in a columnar compartment above the working electrode of an ECL system. Sufficient dwell time in the cell must be provided to permit the particles to settle on the surface of the electrode before inducing ECL.

In another embodiment of the invention, the assay composition containing suspended particles having a density greater than the balance of the assay composition may be subjected to centrifugation in order to remove the particles to a measurement zone where they are subsequently brought into contact with, e.g., an electrode to induce electrochemiluminescence or brought directly into contact with an electrode in the centrifugation step.

In this embodiment, the measurement cell is provided with means to rapidly rotate the sample and sample enclosure. Centrifugal force causes the particles in the sample to move outward from the axis of rotation of the sample enclosure and to collect on the outer surface of the sample enclosure. The outer surfaces of such sample enclosure may constitute the working electrode of an ECL measurement system.

In a third embodiment, the particles may be removed by filtration from the assay composition. In this embodiment the particles need not have a density greater than the balance of the assay composition. The invention, the particles are separated from the solution and concentrated by drawing the solution through a filter, e.g. pumping and collecting the particles on the surface of the filter. This surface of the filter is, for example, coated with a thin metal film which can serve as the working electrode in an ECL detection system.

In a preferred embodiment, the suspended particles are magnetically responsive, e.g. they may be paramagnetic or ferromagnetic, and are collected in a measurement zone or, preferably, directly at the surface of an electrode, by imposition of a magnetic field on the particles. The measurement cell is equipped with a magnet. The magnetic field of the magnet applies a force on the particles as they reside in a batch cell or as they flow through a flow cell, causing them to separate from the bulk of the solution onto the surface of the cell which is in closest proximity to the magnet. If the magnet is placed in a proper orientation and in close proximity to the working electrode of an ECL detection system the particles will concentrate on the surface of the working electrode.

Several different heterogeneous and homogeneous formats for binding assays can be implemented using the methods described above to collect and concentrate the complex on the surface of an electrode. In a heterogeneous binding assay the complex is separated from the composition before measuring luminescence from the label. In homogeneous assays, no separation of the bound (to the solid phase) and unbound labeled reagents is made.

In a homogeneous assay, when the complex is concentrated on the surface of the working electrode, the measured signal from the label is much greater than it would be in the absence of a collection step. The signal from the uncomplexed labeled reagents, in contrast, is not changed. Hence, despite the presence of the uncomplexed labeled reagents in the measurement cell, the signal from the collected complex is stronger than in an assay without collection of complex. The detection limit for the binding assay is, much improved as a result of the collection procedure.

In a preferred embodiment of the invention, an in-situ separation step is included in the homogeneous binding assay procedure. After the assay composition, i.e., sample, assay performance substance and particles have been pumped into the measurement cell and the complex captured upon the working electrode, a second fluid is pumped through the cell which is free of label or labeled reagents, thereby performing an in-situ wash or separation of the complex from unbound components of the assay composition. This assay procedure is technically a heterogeneous binding assay. However, the ability to perform the separation inside the measurement cell is advantageous in that it does not require additional separation apparatus and the procedure is generally much faster than external separation methods.

Heterogeneous binding assays are conducted using the invention by mixing the components of the assay composition and allowing them to react for a predetermined length of time. The assay composition is then subjected to a separation step wherein the solution is separated from the particles. Electrochemiluminescence is then measured from either the complex or the solution. Measuring the ECL from the complex after a concentration step permits measurement of analyte with better accuracy and with a lower detection limit than is possible without concentration.

DETAILED DESCRIPTION OF THE INVENTION

The invention, as well as other objects and features thereof, will be understood more clearly and fully from the following description of certain preferred embodiments.

The invention is broadly applicable to analytes of interest which are capable of entering into binding reactions. These reactions include, e.g., antigen-antibody, ligand receptor, DNA and RNA interactions, and other known reactions. The invention relates to different methods and assays for qualitatively and quantitatively detecting the presence of such analytes of interest in a multicomponent sample.

The Samples

The sample which may contain the analyte of interest, which may be in solid, emulsion, suspension, liquid, or gas form, may be derived from, for example, cells and cell-derived products, water, food, blood, serum, hair, sweat, urine, feces, tissue, saliva, oils, organic solvents or air. The sample may further comprise, for example, water, acetonitrile, dimethyl sulfoxide, dimethyl formamide, n-methyl-pyrrolidone or alcohols or mixtures thereof.

The Analytes

Typical analytes of interest are a whole cell or surface antigen, subcellular particle, virus, prion, viroid, antibody, antigen, hapten, fatty acid, nucleic acid, protein, lipoprotein, polysaccharide, lipopolysaccharide, glycoprotein, peptide, polypeptide, cellular metabolite, hormone, pharmacological agent, synthetic organic molecule, organometallic molecule, tranquilizer, barbiturate, alkaloid, steroid, vitamin, amino acid, sugar, lectin, recombinant or derived protein, biotin, avidin, streptavidin, or inorganic molecule present in the sample. Typically, the analyte of interest is present at a concentration of $10^{-3}$ molar or less, for example, as low as $10^{-12}$ molar or lower.

Assay-Performance-Substance

The assay-performance-substance which is combined with the sample containing the analyte of interest contains at least one substance selected from the group consisting of (i) added analyte of interest or its analog, as defined above, (ii) a binding partner of the analyte of interest or its said analog, and (iii) a reactive component, as defined above, capable of binding with (i) or (ii), wherein one of said substances is linked to a compound or moiety, e.g. an ECL moiety capable of being induced to luminesce. The labeled substance may be a whole cell or surface antigen, a subcellular particle, virus, prion, viroid, antibody, antigen, hapten, lipid, fatty acid, nucleic acid, polysaccharide, protein, lipoprotein, lipopolysaccharide glycoprotein, peptide, polypeptide, cellular metabolite, hormone, pharmacological agent, tranquilizer, barbiturate, alkaloid, steroid, vitamin, amino acid, sugar, nonbiological polymer (preferably soluble), lectin, recombinant or derived protein, synthetic organic molecule, organometallic molecule, inorganic molecule, biotin, avidin or streptavidin. In one embodiment, the reagent is an electrochemiluminescent moiety conjugated to an antibody, antigen, nucleic acid, hapten, small nucleotide sequence, oligomer, ligand, enzyme, or biotin, avidin, streptavidin, Protein A, Protein G, or complexes thereof, or other secondary binding partner capable of binding to a primary binding partner through protein interactions.

Analogs of the analyte of interest, which can be natural or synthetic, are typically compounds which have binding properties comparable to the analyte, but can also be compounds of higher or lower binding capability. The reactive components capable of binding with the analyte or its analog, and/or with a binding partner thereof, and through which the ECL moiety can be linked to the analyte, is suitably a second antibody or a protein such as Protein A or Protein G, or avidin or biotin or another component known in the art to enter into binding reactions.

The Labels

Advantageously, the ECL moieties are metal chelates. The metal of that chelate is suitably any metal such that the metal chelate will luminesce under the electrochemical conditions which are imposed on the reaction system in question. The metal of such metal chelates is, for instance, a transition metal (such as a d-block transition metal) or a rare earth metal. The metal is preferably ruthenium, osmium, rhenium, iridium, rhodium, platinum, indium, palladium, molybdenum, technetium, copper, chromium or tungsten. Especially preferred are ruthenium and osmium.

The ligands which are linked to the metal in such chelates are usually heterocyclic or organic in nature, and play a role in determining whether or not the metal chelate is soluble in an aqueous environment or in an organic or other nonaqueous environment. The ligands can be polydentate, and can be substituted. Polydentate ligands include aromatic and aliphatic ligands. Suitable aromatic polydentate ligands include aromatic heterocyclic ligands. Preferred aromatic heterocyclic ligands are nitrogen-containing, such as, for example, bipyridyl, bipyrazyl, terpyridyl, and phenanthrolyl. Suitable substituents include for example, alkyl, substituted alkyl, aryl, substituted aryl, aralkyl, substituted aralkyl, carboxylate, carboxaldehyde, carboxamide, cyano, amino, hydroxy, imino, hydroxycarbonyl, aminocarbonyl, amidine, guanidinium, ureide, sulfur-containing groups, phosphorus containing groups, and the carboxylate ester of N-hydroxysuccinimide. The chelate may have one or more monodentate ligands, a wide variety of which are known to the art. Suitable monodentate ligands include, for example, carbon monoxide, cyanides, isocyanides, halides, and aliphatic, aromatic and heterocyclic phosphines, amines, stilbenes, and arsines.

Examples of suitable chelates are bis [(4,4'-carbomethoxy)-2,2'-bipyridine] 2-[3-(4-methyl-2,2'-bipyridine-4-yl)propyl]-1,3-dioxolane ruthenium (II); bis (2,2'bipyridine) [4-(butan-1-al)-4'-methyl-2,2'-bipyridine] ruthenium (II); bis (2,2'-bipyridine) [4-(4'-methyl-2,2'-bipyridine-4'-yl)-butyric acid] ruthenium (II); tris (2,2'bipyridine) ruthenium (II); (2,2'-bipyridine) [bis-bis(1,2-diphenylphosphino) ethylene] 2-[3-(4-methyl-2,2'-bipyridine-4'-yl)propyl]-1,3-dioxolane osmium (II); bis (2,2'-bipyridine) [4-(4'-methyl-2, 2'-bipyridine)-butylamine] ruthenium (II); bis (2,2'-bipyridine) [1-bromo-4(4'-methyl-2,2'-bipyridine-4-yl) butane] ruthenium (II); bis (2,2'-bipyridine) maleimidohexanoic acid, 4-methyl-2,2'-bipyridine-4'-butylamide ruthenium (II). Other ECL moieties are described in commonly assigned PCT published application US87/00987 and PCT published application 88/0394.

The function of the ECL moieties is to emit electromagnetic radiation as a result of introduction into the reaction system of electrochemical energy. In order to do this, they must be capable of being stimulated to an excited energy state and also capable of emitting electromagnetic radiation, such as a photon of light, upon descending from that excited state. While not wishing to be bound by theoretical analysis of the mechanism of the ECL moiety's participation in the electrochemiluminescent reaction, we believe that it is oxidized by the introduction of electrochemical energy into the reaction system and then, through interaction with a reductant present in the system, is converted to the excited state. This state is relatively unstable, and the metal chelate quickly descends to a more stable state. In so doing, the chelate gives off electromagnetic radiation, such as a photon of light, which is detectable.

The amount of metal chelate or other metal-containing ECL moiety incorporated in accordance with the invention will vary from system to system. Generally, the amount of such moiety utilized is that amount which is effective to result in the emission of a detectable, and if desired, quantitatable, emission of electromagnetic energy, from the aforementioned composition or system. The detection and/or quantitation of an analyte of interest is typically made from a comparison of the luminescence from a sample containing an analyte of interest and an ECL moiety to the luminescence emitted by a calibration standard developed with known amounts of the analyte of interest and ECL moiety. This assumes a homogeneous format. In the heterogeneous mode, a separation as discussed previously is carried out prior to ECL analysis.

As can be appreciated by one of ordinary skill in the art, the identity and amount of the metal-containing ECL moiety will vary from one system to another, depending upon prevailing conditions. The appropriate metal-containing ECL moiety, and sufficient amount thereof to obtain the desired result, can be determined empirically by those of ordinary skill in the art, once equipped with the teachings herein, without undue experimentation.

The Particles

The particles advantageously comprise micro-particulate matter having a diameter of 0.05 um to 200 um, preferably 0.1 um to 100 um, most preferably 0.5 um to 10 um, and a surface component capable of binding to the analyte and/or one or more of the other substances defined in subparagraphs (b) (i), (b) (ii), or (b) (iii) above. For example, the microparticulate matter may be crosslinked starch, dextrans, cellulose, proteins, organic polymers, styrene copolymer such as styrene/butadiene copolymer, acrylonitrile/butadiene/styrene copolymer, vinylacetyl acrylate copolymer, or vinyl chloride/acrylate copolymer, inert inorganic particles, chromium dioxide, oxides of iron, silica, silica mixtures, and proteinaceous matter, or mixtures thereof. Desirably, the particles are suspended in the ECL system.

Assay Media

In order to operate a system in which an electrode introduces electrochemical energy, it is necessary to provide an electrolyte in which the electrode is immersed and which contains the ECL moiety. The electrolyte is a phase through which charge is carried by ions. Generally, the electrolyte is in the liquid phase, and is a solution of one or more salts or other species in water, an organic liquid or mixture of organic liquids, or a mixture of water and one or more organic liquids. However, other forms of electrolyte are also useful in certain embodiments of the invention. For example, the electrolyte may be a dispersion of one or more substances in a fluid—e.g., a liquid, a vapor, or a supercritical fluid—or may be a solution of one or more substances in a solid, a vapor or supercritical fluid.

The electrolyte is suitably a solution of a salt in water. The salt can be a sodium salt or a potassium salt preferably, but incorporation of other cations is also suitable in certain embodiments, as long as the cation does not interfere with the electrochemiluminescent interaction sequence. The salt's anion may be a phosphate, for example, but the use of other anions is also permissible in certain embodiments of the invention—once again, as long as the selected anion does not interfere with the electrochemiluminescent interaction sequence.

The composition may also be nonaqueous. While supercritical fluids can in certain instances be employed advantageously, it is more typical to utilize an electrolyte comprising an organic liquid in a nonaqueous composition. Like an aqueous electrolyte, the nonaqueous electrolyte is also a phase through which charge is carried by ions. Normally, this means that a salt is dissolved in the organic liquid medium. Examples of suitable organic liquids are acetonitrile, dimethylsulfoxide (DMSO), dimethylformamide (DMF), methanol, ethanol, and mixtures of two or more of the foregoing. Illustratively, tetraalkylammonium salts, such as tetrabutylammonium tetrafluoroborate, which are soluble in organic liquids can be used with them to form nonaqueous electrolytes.

The electrolyte is, in certain embodiments of the invention, a buffered system. Phosphate buffers are often advantageous. Examples are an aqueous solution of sodium phosphate/sodium chloride, and an aqueous solution of sodium phosphate/sodium fluoride.

Other Assay Components

As described PCT published application U.S. 89/04859 commonly assigned, entitled Electrochemiluminescent Reaction Utilizing Amine-Derived Reductant, the disclosure of which is incorporated by reference, it is desirable to include a reductant, typically an amine or amine moiety (of a larger molecule) which can be oxidized and spontaneously decomposed to convert it into a highly reducing species. It is believed that the amine or amine moiety is also oxidized by electrochemical energy introduced into the reaction system. The amine or amine moiety loses one electron, and then deprotonates, or rearranges itself, into a strong reducing agent. This agent interacts with the oxidized metal-containing ECL moiety and causes it to assume the excited state discussed above. In order to carry out its role, the amine or amine moiety preferably has a carbon-centered radical with an electron which can be donated from such carbon, and an alpha carbon which can then act as a proton donor during deprotonation in order to form the reductant. The amine-derived reductant provides the necessary stimulus for converting the metal-containing ECL moiety to its excited state, from which detectable electromagnetic radiation is emitted.

A wide range of amines and corresponding amine moieties can be utilized in practicing the present invention. Generally, the amine or amine moiety is chosen to suit the pH of the system which is to be electrochemiluminescently analyzed. Another relevant factor is that the amine or amine moiety should be compatible with the environment in which it must function during analysis, i.e., compatible with an aqueous or nonaqueous environment, as the case may be. Yet another consideration is that the amine or amine moiety selected should form an amine-derived reductant under prevailing conditions which is strong enough to reduce the oxidized metal-containing ECL moiety in the system.

Amines (and corresponding moieties derived therefrom) which are advantageously utilized in the present invention are aliphatic amines, such as primary, secondary and tertiary alkyl amines, the alkyl groups of each having from one to three carbon atoms, as well as substituted aliphatic amines. Tripropyl amine is an especially preferred amine as it leads to, comparatively speaking, a particularly high-intensity emission of electromagnetic radiation, which enhances the sensitivity and accuracy of detection and quantitation with embodiments in which it is used. Also suitable are diamines, such as hydrazine, and polymines, such as poly(ethyleneimine). Examples of other amines suitable for practicing the invention are triethanol amine, triethyl amine, 1,4-diazabicyclo-(2.2.2)-octane, 1-piperidine ethanol, 1,4-piperazine-bis-(ethane-sulfonic acid), tri-ispropyl amine and poly(ethyleneimine).

Typically, the metal-containing ECL moiety utilized in the present invention is the reaction-limiting constituent. Accordingly, it is also typical that the amine or amine moiety is provided in a stoichiometric excess with respect thereto.

Illustratively, the amine or amine moiety is employed in a concentration of 50-150 mM. For utilization at a pH of approximately 7, a concentration of 100 mM is often advantageous. In certain embodiments, the upper limit on amine or amine moiety concentration is determined by the maximum solubility of the amine or moiety in the environment in which it is being used, for example in water. In general, the amount of amine or amine moiety employed is that which is sufficient to effect the transformation of the oxidized metal-containing ECL moiety into its excited state so that luminescence occurs. Those of ordinary skill in the art, equipped with the teachings herein, can determine empirically the amount of amine or amine moiety advantageously used for the particular system being analyzed, without undue experimentation.

As described in commonly assigned PCT published application US 89/04915, entitled Enhanced Electrochemiluminescent Reaction, the contents of which are incorporated by reference, the assays of the invention are desirably carried out in the presence of an enhancer, typically a compound of the formula

wherein R is hydrogen or $C_nH_{n2+1}$, R' is $C_nH_{2n}$, x is 0 to 70, and n is from 1 to 20. Specifically, n is from 1 to 4. Specific examples are a substance available in commerce under the name Triton X-100, of the formula

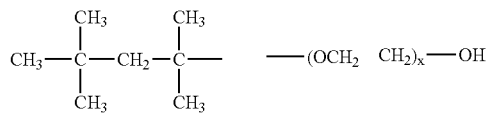

wherein x is 9-10, and a substance available in commerce under the name Triton N-401 (NPE-40), of the formula

wherein x is 40. The enhancer is generally utilized in an amount sufficient so that in its presence the desired increase in emission of electromagnetic radiation occurs. Typically, the amount is 0.01% to 5.0%, more specifically 0.1% to 1.0%, v/v. The subject matter of this application is incorporated by reference.

The ECL moiety incorporated in accordance with the present invention is induced to emit electromagnetic radiation by stimulating it into an excited state. This is accomplished by exposing the system in which the ECL moiety is incorporated to electrochemical energy. The potential at which oxidation of the ECL moiety and the species forming a strong reductant occurs depends upon the exact chemical structures thereof, as well as factors such as the pH of the system and the nature of the electrode used to introduce electrochemical energy. It is well known to those of ordinary skill in the art how to determine the optimal potential and emission wavelength of an electrochemiluminescent system. Certain preferred methods of stimulating the ECL system are disclosed in commonly assigned PCT published application US 89/01814, the contents of which are incorporated herein by reference.

Apparatus for Measuring Electrochemiluminescence

Figure 2:
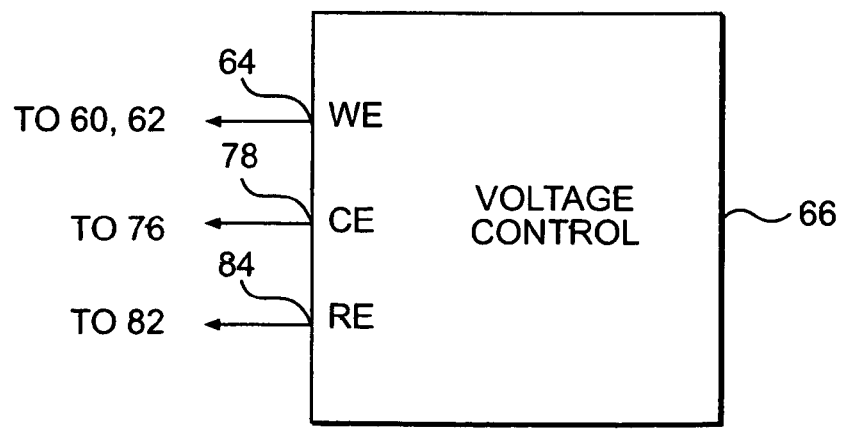
FIG. 2 is a simplified diagram of a voltage control apparatus for use with the cell of FIG. 1.

An apparatus for carrying out the assays of the invention is described in FIGS. 1 and 2. FIG. 1 discloses an advantageous ECL apparatus, but the methods of the present invention are not limited to application in apparatus 10, but rather may be employed in other types of ECL apparatus which include a working electrode or other triggering surface to provide electrochemical energy to trigger the ECL moiety into electrochemiluminescence. While the methods of the invention can be carried out in a static or flow-through mode, apparatus 10 includes a flow-through cell, which provides distinct advantages for many types of samples including binding assay samples. Further details of apparatus for carrying out the ECL assays of the invention are disclosed in commonly assigned published PCT applications US 89/04854 and U.S. 90/01370.

Apparatus 10 includes an electrochemical cell 12, a light detection/measurement device 14, which may advantageously be a photomultiplier tube (PMT), photodiode, charge coupled device, photographic film or emulsion or the like, and a pump 16, which is advantageously a peristaltic pump, to provide for fluid transport to, through and from cell 12. Alternatively, a positive displacement pump may be used. A shutter mechanism 18 is provided between cell 12 and PMT 14 and is controllably operated to open only so far as to expose PMT 14 to cell 12 during ECL measurement periods. The shutter mechanism may be closed, for example, during maintenance. Also included in apparatus 10 but not illustrated in FIG. 1 is a lightproof housing intended to mount the various components therein and to shield PMT 14 from any external light during the ECL measurements.

Cell 12 itself includes a first mounting block 20 through which passes an inlet tube 22 and an outlet tube 24, which may be advantageously constructed of stainless steel. Mounting block 20 has a first, outer surface 26 and a second, inner surface 28 defining one side of a sample-holding volume 30 of cell 12 in which cell 12 holds the cleaning and/or conditioning and/or measurement solutions during corresponding operations of apparatus 10. Inlet and outlet tubes 22, 24 pass through mounting block 20 from outer surface 26 to inner surface 28 and open into sample-holding volume 30. A second mounting block 32, advantageously constructed of stainless steel also has a first, outer surface 34 and a second, inner surface 36. Second mounting block 32 is separated from first mounting block 20 by an annular spacer 38, advantageously constructed of Teflon or other non-contaminable material. Thus, outer surface 34 of mounting block 30 defines part of the second side of the sample-holding volume 30. Spacer 38 has an outer portion 40 and a central aperture 42 whose inner edge 44 defines the side wall of sample-holding volume 30. Outer portion 40 seals the inner surface 28 of first mounting block 20 to outer surface 34 of second mounting block 32 to prevent any solution from passing out from sample-holding volume 30 between the two surfaces 28, 34. Mounting block 32 further has a central aperture 46 in which a window 48 is seal-fitted to define the rest of the second side of sample-holding volume 30 as a continuation of outer surface 34.

Window 48 is formed of a material which is substantially transparent at the wavelength of electrochemiluminescent light emitted by the ECL moiety. Window 48 is therefore advantageously formed of glass, plastic, quartz or the like.

Inlet tube 22 intersects sample-holding volume 30 at a first end 50 thereof adjacent to spacer 38 and outlet tube 24 intersects sample-holding volume 30 at a second end 52 thereof, adjacent spacer 38. The combination of inlet tube 22, sample-holding volume 30 and outlet tube 24 thereby provides a continuous flow path for the narrow, substantially laminar flow of a solution to, through and from cell 12.

Mounted on inner surface 28 of first mounting block 20 is a working electrode system 54 which, in the illustrated embodiment, includes first and second working electrodes 56 and 58. In other embodiments, a single working electrode may advantageously be provided, or only electrode 56 may be a working electrode. Working electrodes 56, 58 are where the electrochemical and ECL reactions of interest can take place. Working electrodes 56, 58 are solid voltammetric electrodes and may therefore be advantageously constructed of platinum, gold, carbons or other materials which are effective for this purpose. Wire connectors 60, 62 connected to working electrodes 56, 58, respectively, pass out through first mounting block 20.

Connectors 60, 62 are both connected to a first, "working electrode" terminal 64 of a voltage control 66, illustrated in FIG. 2. Voltage control 66 advantageously operates in the manner of a potentiostat to supply voltage signals to working electrodes 56, 58 and optionally to measure current flowing therefrom during an ECL measurement. Alternatively, connectors 60, 62 may be connected to separate terminals of voltage control 66 for individual operation.

The potentiostat operation of voltage control 66 is further effected through a counter electrode 68 and, optionally but advantageously, a reference electrode 70. In the illustrated embodiment, mounting block 32 is made of stainless steel and counter electrode 68 consists in exposed surfaces 72, 74 of mounting block 32. Counter electrode 72, 74 and working electrodes 56, 58 provide the interface to impress the potential on the solution within sample-holding volume 30 which energizes the chemical reactions and triggers electrochemiluminescence in the sample and/or provides energy for cleaning and conditioning the surfaces of cell 12. Counter electrode 72, 74 is connected by a wire connector 76 to a second, "counter electrode" terminal 78 of voltage control 66.

Reference electrode 70 provides a reference voltage to which the voltage applied by the working electrodes 56, 58 is referred, for example, +1.2 volts versus the reference. Reference electrode 70 is advantageously located in outlet tube 24 at a position 80 spaced from cell 12 and is connected through a wire connector 82 to a third "reference electrode" terminal 84 of voltage control 66. In the three electrode mode, current does not flow through reference electrode 70. Reference electrode 70 may be used in a three electrode mode of operation to provide a poised, known and stable voltage and is therefore advantageously constructed of silver/silver chloride (Ag/AgCl) or is a saturated calomel electrode (SCE). Voltage control 66 may be operable in a two electrode mode of operation using only working electrode 56 and electrode 58 as a counter/reference electrode. In this two electrode mode of operation, counter/reference electrode 58 is electrically connected to voltage control terminals 78 and 84 on voltage control 66. In this case, voltage control 66 operates essentially as a battery. Voltage control 66 supplies voltage signals to working and counter electrodes 56 and 58 and optionally measures the current flowing through the respective electrodes. Reference electrode 70 may alternatively be a so-called "quasi-reference" electrode constructed of platinum, gold, stainless steel or other material, which provides a less stable voltage, yet one that is measurable with respect to the solution in contact. In both the two and three electrode mode, the reference electrode 70 or 58 serves the purpose of providing a reference against which the voltage applied to working electrodes 56 is measured. The poised voltage reference is currently considered to be more advantageous. Voltage control 66 in its potentiostat operation controls the various electrodes by providing a known voltage at working electrodes 56, 58 with respect to reference electrode 70 while measuring the current flow between working electrodes 56, 58 and counter electrode 72, 74. Potentiostats for this purpose are well known, and the internal structure of voltage control 66 may therefore correspond to any of the conventional, commercially available potentiostats which produce the above-recited functions and so do not form a part of the present invention per se. Indeed, apparatus 10 may alternatively be constructed without an internal voltage control 66, and may be adapted to be connected to an external potentiostat which is separately controlled for providing the required voltage signals to electrodes 56, 58, 72, 74 and 70. These voltage signals, applied in a specific manner as described below, provide repeatable initial conditions for the surfaces of working electrodes 56, 58 and advantageously for the surfaces of cell 12 as a whole, a feature which contributes significantly to improved precision in ECL measurements.

Pump 16 is advantageously positioned at outlet tube 24 to "pull" solution from a sample volume in the direction of arrow A into inlet tube 22. The solution will flow through inlet tube 22, sample-holding volume 30 and outlet tube 24 past reference electrode 70 and out in the direction of arrow B. Alternatively, pump 16 may be positioned at inlet tube 22 to "push" the solution through apparatus 10. Advantageously, this same flow path through inlet tube 22, sample-holding volume 30 and outlet tube 24 is used for all solutions and fluids which pass through cell 12, whereby each fluid performs a hydrodynamic cleaning action in forcing the previous fluid out of cell 12. Pump 16 may be controlled to suspend its operation to hold a particular solution in cell 12 for any period of time.

The flow-through construction of apparatus 10 permits working electrodes to be impressed with a variable voltage or to be continuously held at a preoperative potential while being continuously exposed to one or more solutions without exposing working electrodes 56, 58 (or counter and reference electrodes 72, 74, 70) to air. Exposure to air, which opens the circuit to the reference electrode 70, permits unknown, random voltage fluctuations which destroy the reproducibility of surface conditions on working electrodes 56, 58. The flow-through construction permits the rapid alternation between initializing steps, in which electrode system 54 is cleaned and conditioned, and measurement steps, in which one or more measurement waveforms or sweeps trigger ECL.

The invention is also directed to reagent compositions. Broadly, the reagent compositions may be any one of the components of the assay systems of the invention, i.e., (a) electrolyte, (b) label compound containing an ECL moiety, (c) particles, including magnetically responsive particles, (d) analyte of interest or an analog of the analyte of interest, (e) a binding partner of the analyte of interest or of its analog, (f) a reactive component capable of reacting with (d) or (e), (g) a reductant, or (h) an electrochemiluminescence-reaction enhancer. The reagents may be combined with one another for convenience of use, i.e., two component, three component, and higher multiple component mixtures may be prepared, provided that the components are not reactive with one another during storage so as to impair their function in the intended assay. Desirably, the reagents are two-component or multicomponent mixtures which contain particles as well as one or more other components.

The invention is also directed to kits. The kits may include vessels containing one or more of the components (a) to (h) recited above or the kits may contain vessels containing one or more reagent compositions as described above comprising mixtures of those components, all for use in the assay methods and systems of the invention.

DESCRIPTION OF PREFERRED EMBODIMENTS OF THE INVENTION

While a wide range of particles can be employed in the particle-based assays of the invention, generally the particles have a density of from 1.0 to 5.0 g/mL and preferably have a density of from 1.1 to 2 g/mL. Choice of the optimum density is within the skill of the art, the rate of settling in gravity-driven assays being a trade-off between the speed of the assay and the desire to create a uniform layer of complex on the electrode surface.

Particles having a wide range of mean diameters can also be employed. Particles having a mean diameter of from 0.001 to 100 μm can be used and preferably the particles have a mean diameter of from 0.01 to 10 μm.

Wide ranges of concentration of particles in the assay composition can also be employed. For example, the concentration can range from 1 to 10,000 μg/mL to preferably from 5 to 1000 μg/mL. Desirably, the density of the particles, their size and their concentration is selected such that the particles settle at a rate of at least 0.5 mm/min and preferably at a faster rate.

In the filtration mode of performing the invention, the filtration means desirably has a pore size, measured as mean diameter, from broadly 0.01 to 90% of the mean diameter of the particles and preferably from 10% to 90% of that diameter.

The art has described a number of magnetic particles which can be used in the assays of the invention. For example, U.S. Pat. Nos. 4,628,037, 4,695,392, 4,695,393, 4,698,302, 4,554, 088, U.K. Patent Application GB 2,005,019A and EP 0,180, 384, describe a variety of magnetic particles which can be used with success. The particles may be paramagnetic or ferromagnetic and may be coated with various materials to which binding compounds are coupled so that the magnetic particle can be used in immunoassays. Desirably the magnetic particles used in the invention have a susceptibility of at least 0.001 cgs units and desirably the susceptibility is at least 0.01 cgs units. The magnetic particles may have a broad range of densities, i.e. from substantially less than that of water, 0.01, to 5 g/mL and preferably from 0.5 to 2 g/mL. The particle sizes can range from 0.001 to 100 μm and preferably from 0.01 to 10 μm. The concentration of the particles may range broadly from 1 to 10,000 μg per mL and preferably is from 5 to 1000 μg per mL.

Desirably the magnetic particles which are used have a low magnetic remanence, as described for example EP 0,180,384, so that after the magnetic field is removed from the electrode surface, the particles demagnetize and can be swept out of the assay cell. Desirably the density, concentration and particle size of the magnetic particles is chosen such that the settling time is at least 0.5 mm/min and desirably it is above that rate. In operation of the magnetic cell it is often desirable to remove the magnet means from the electrode surface prior to inducing electrochemiluminescence in order not to interfere with the operation of the photomultiplier tube.

Assays

A variety of assays can be performed using the methods of the invention.

Figure 3:
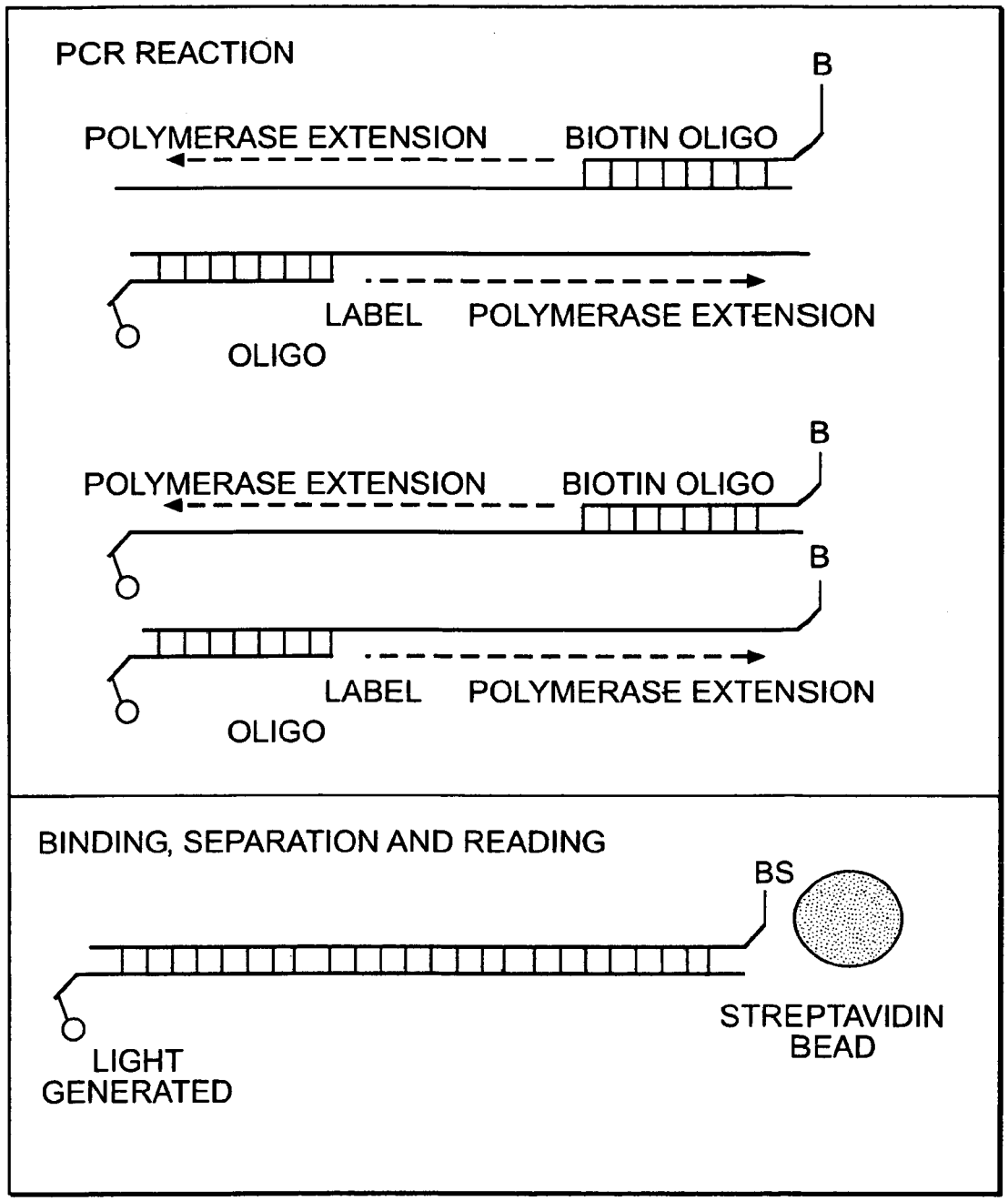
FIG. 3 is a schematic representation of a direct incorporation PCR format using electrochemiluminescent labeled oligonucleotides and biotin electrochemiluminescent labeled oligonucleotides as primers.

An assay was performed as shown in FIG. 3. The PCR products resulting from the reaction were labeled with biotin and an ECL label (tris (2,2' bipyridine) Ru II, Ru $(bpy)_3^{2+}$). Streptavidin beads captured the bifunctionalized DNA via biotin streptavidin binding and this was followed by washing. The bead bound product was then subjected to analysis detecting the ECL label.

Figure 4:
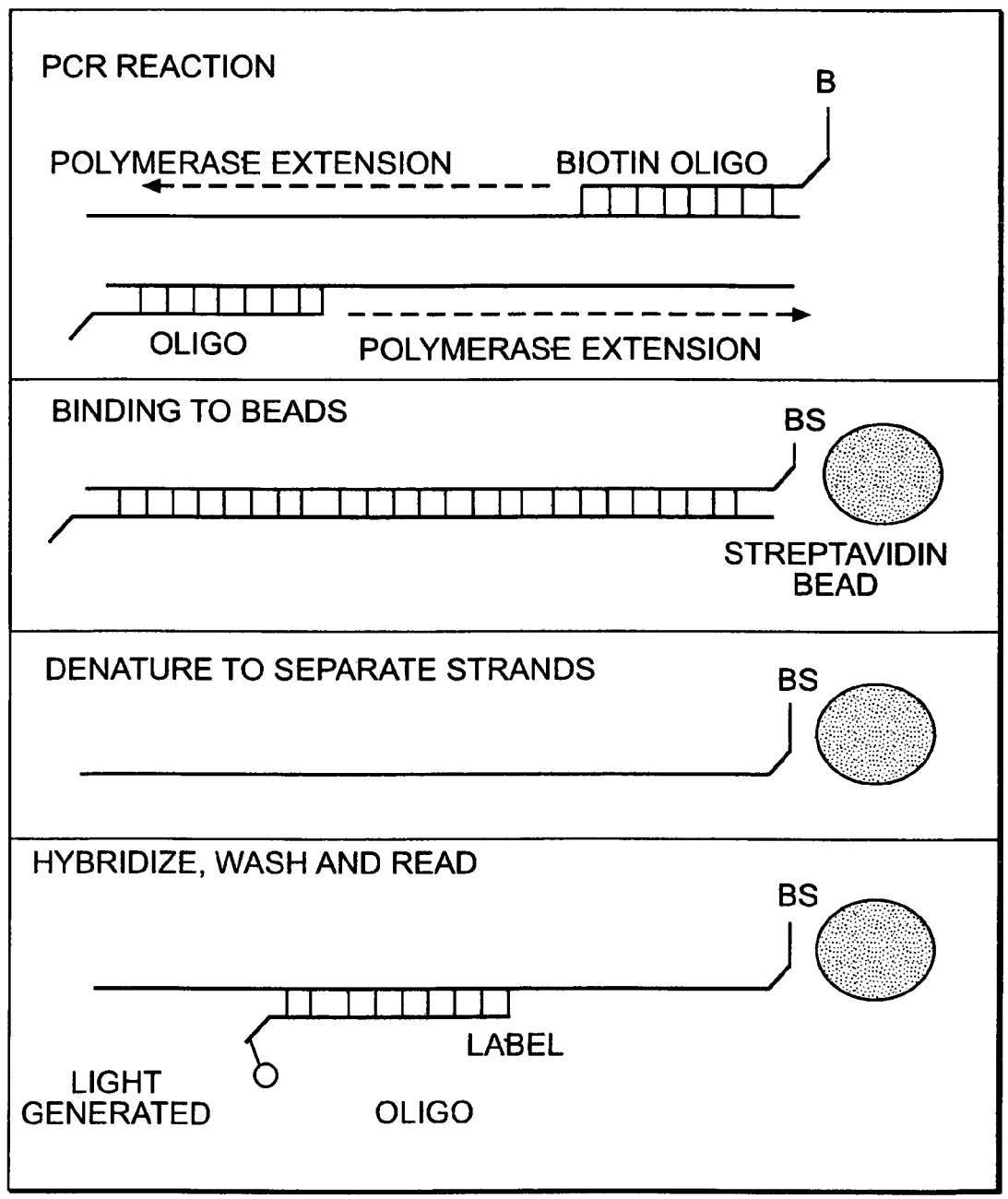
FIG. 4 is a schematic representation of a normal PCR format using a biotinylated primer to allow the generation of biotinylated PCR and PRODUCT.

An assay was performed as shown in FIG. 4. The biotinylated PCR product was captured on streptavidin beads and the non-biotinylated strand removed. The bead bound PCR product was then hybridized with an ECL labeled (Ru $(bpy)_3^{2+}$)-oligonucleotide. This was followed by ECL analysis to detect the label.

Figure 5:
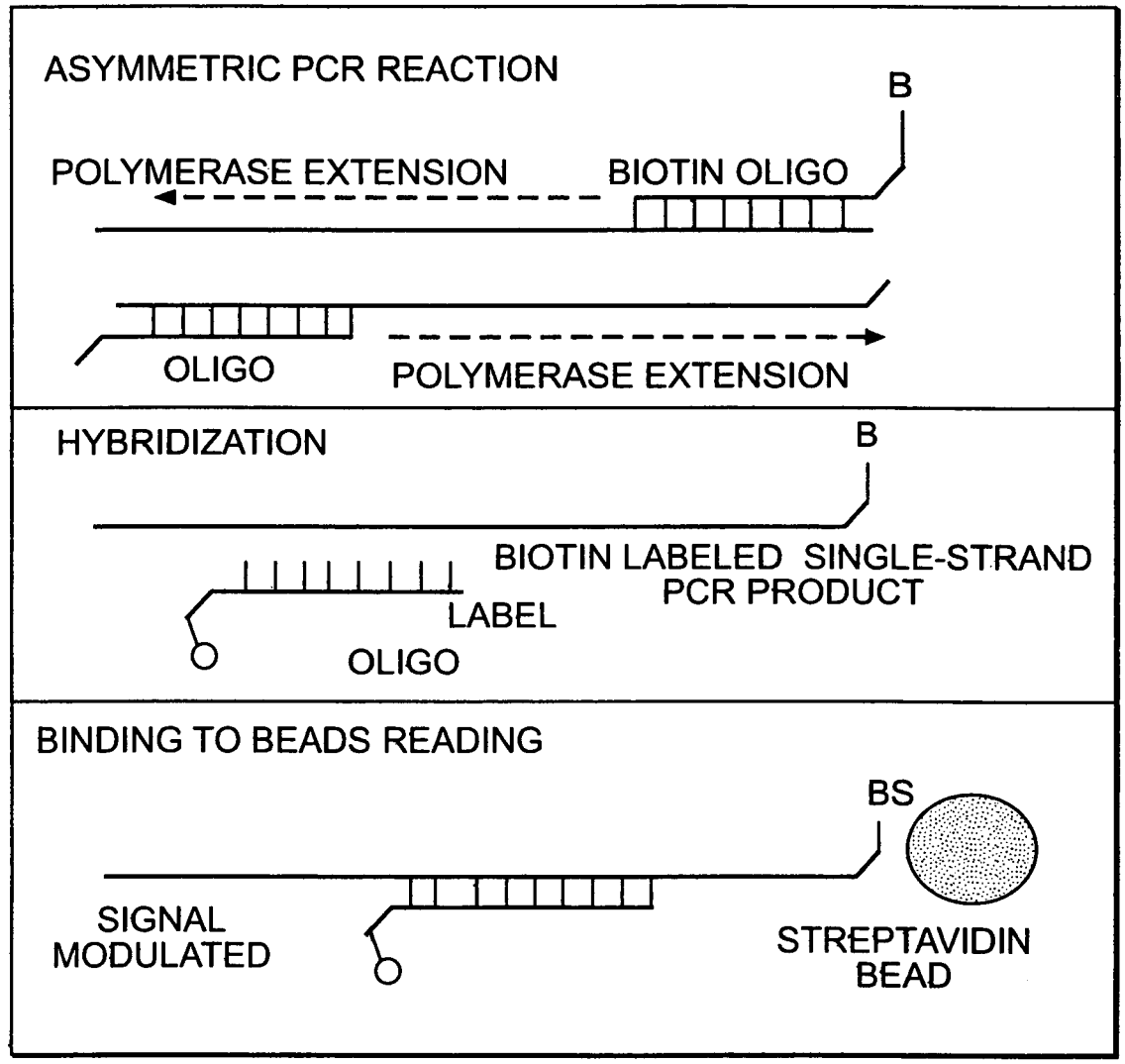
FIG. 5 is a schematic representation of an asymmetric PRC assay format generating single-stranded biotinylated DNA for later hybridization to electrochemiluminescent labeled oligonucleotides.

An assay was conducted as shown in FIG. 5. The hybrids were captured on streptavidin beads. This was followed by ECL analysis without washing.

Figure 6:
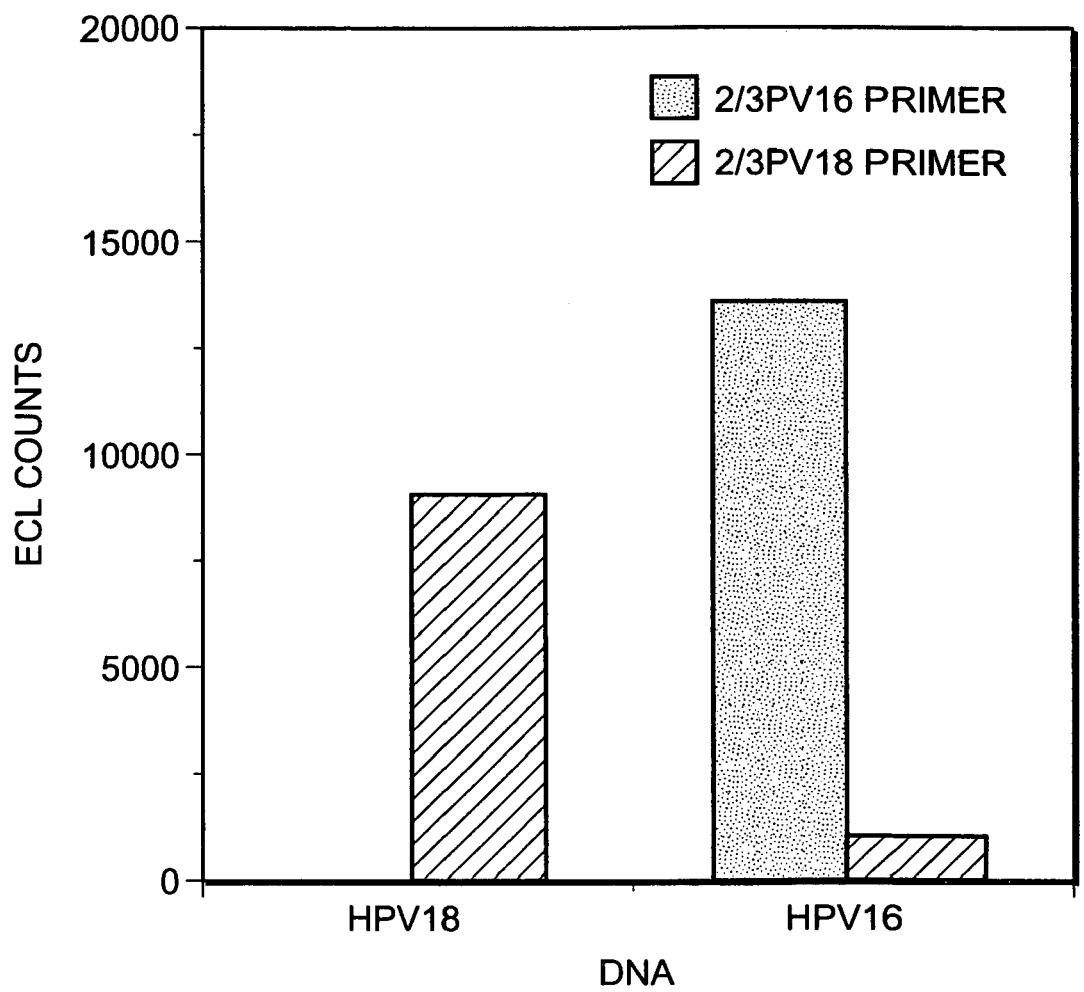
FIG. 6 is a graph showing specificity studies of the direct incorporation of electrochemiluminescent labeled oligonucleotides into biotinylated PCR products.

An assay was conducted and the results are shown in FIG. 6. The assay was for the presence of HPV 16 and 18 using DNA samples isolated from the cell lines SiHa and HeLa positive for both virus types and oligonucleotides specific for each virus type. The primers 2PV16, 2PV18 were biotinylated and 3PV16, 3PV18 were ECL-labeled-oligonucleotides. The 2/3PV16 and 2/3PV18 oligonucleotides were specific for HPV 16 and 18 respectively. The resultant bead captured ECL label was analyzed for ECL using an analyzer as described in FIG. 1. The results were plotted as ECL counts for each sample primer combination.

Figure 7:
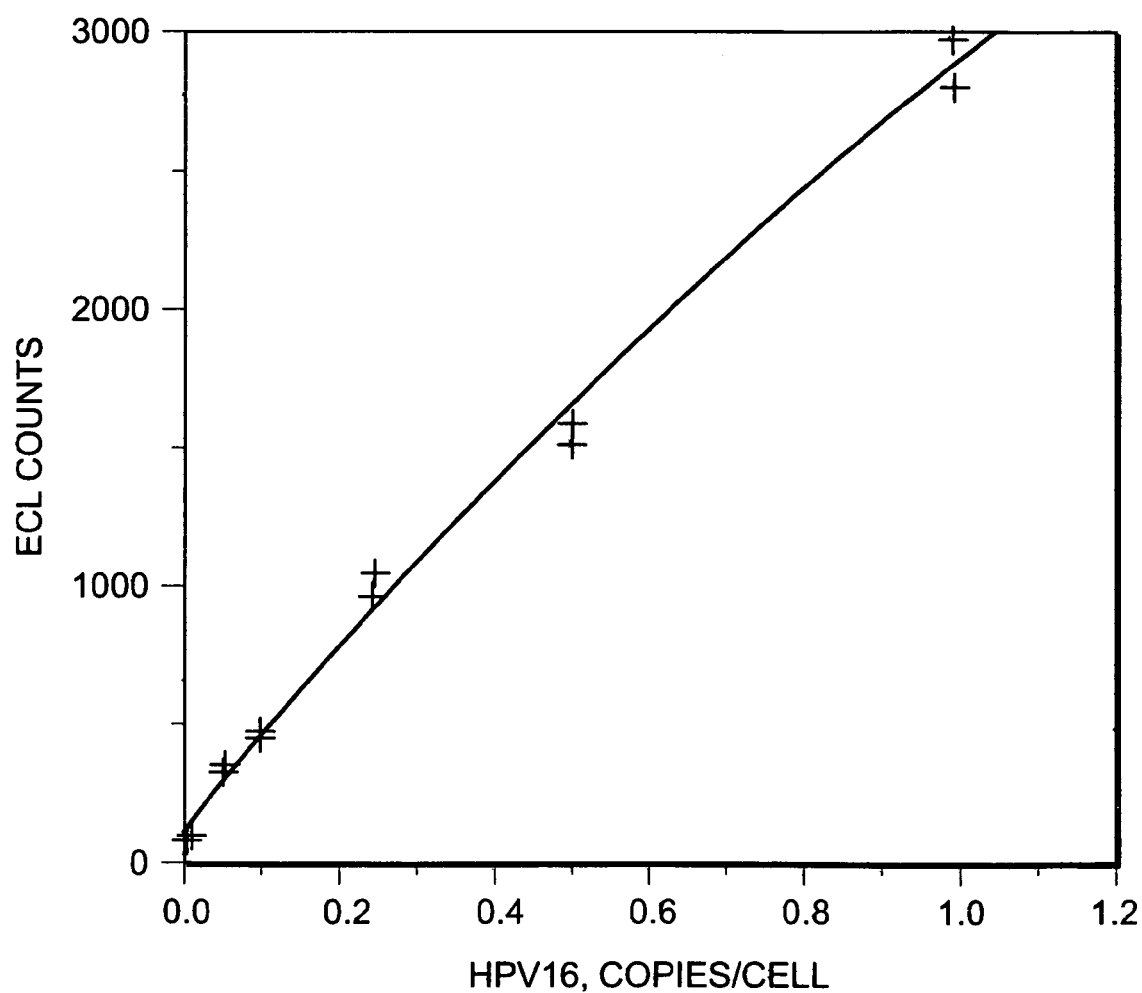
FIG. 7 is a standard curve of directly incorporated electrochemiluminescent label and biotinylated oligonucleotides into HPV16 PCR products.

An assay was conducted and the results are shown in FIG. 7. The resultant bead bound ECL label was analyzed for ECL using an analyzer as described in FIG. 1. The ECL peak photon counts were plotted against increasing concentrations HPV 16 DNA, expressed as a ratio of viral copies to total cellular DNA copies. The primers used in this analysis for HPV16 were 1PV16 (biotin label) and 2PV16 (ECL label). DNA used for each PCR was maintained at a constant 1 μg using calf thymus DNA.

Figure 8:
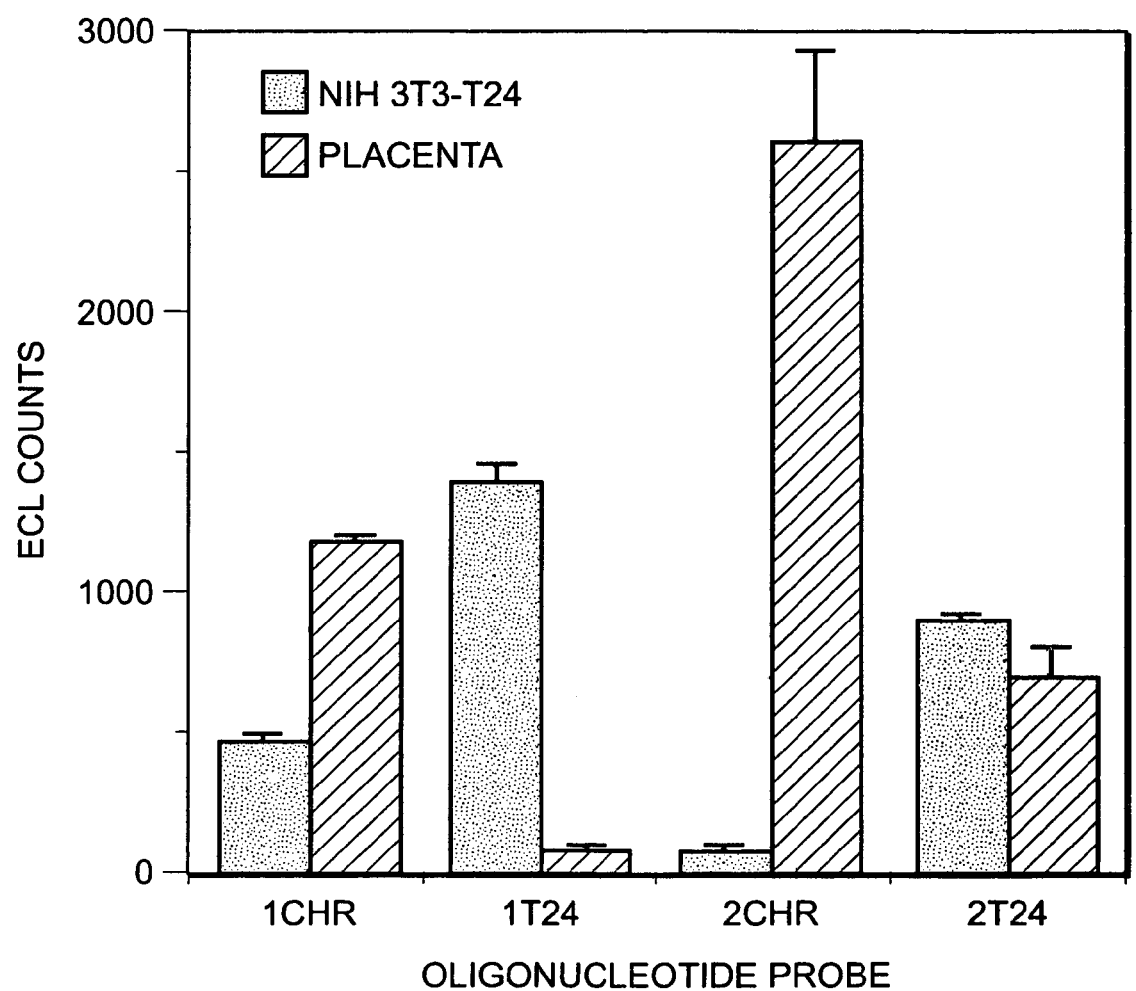
FIG. 8 is a graph showing a point mutation assay for the Ha-ras oncogene.

An assay was conducted and the results are shown in FIG. 8. The PCR was performed using biotinylated HRP2 with unlabeled HRP1 (for probes 1T24 and 1CHR) and biotinylated HRP1 with unlabeled HRP2 (for probes 2T24 and 2CHR), generating bead bound single stranded targets for hybridization. The DNA samples were the normal (Placenta) Ha-ras Gene and the mutant (NIH3T3-T24) Ha-ras Gene. The hybridization of the bead bound DNA with ECL label-1T24 (1T24), ECL label-2T24 (2T24), ECL label-1CHR (1CHR) and ECL label-2CHR (2CHR) was followed by TEMAC washes. Resultant bead bound ECL label was analyzed for ECL using an analyzer as described in FIG. 1. Results were plotted as ECL counts for each sample probe combination.

Figure 9:
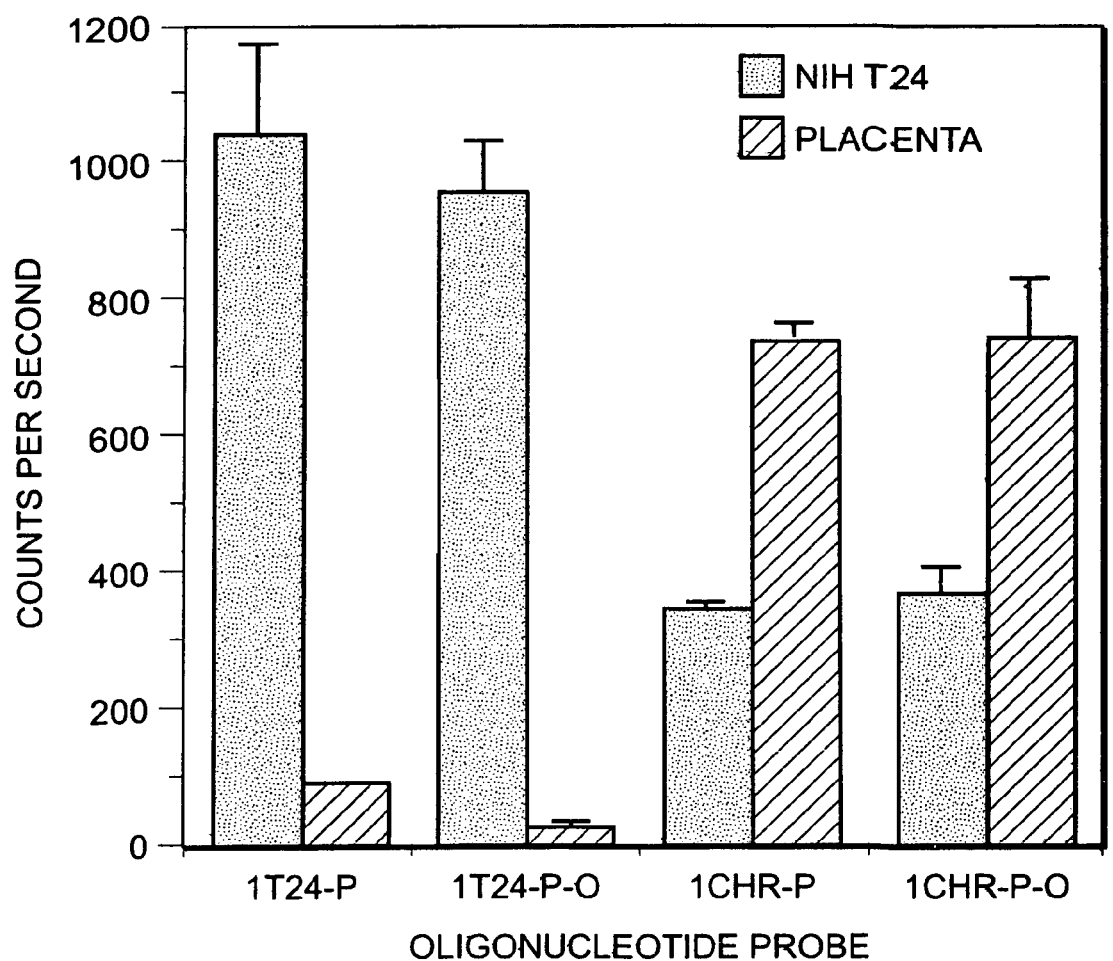
FIG. 9 is a graph showing an evaluation of the specificity of electrochemiluminescent labeled probes using $P^{32}$ electrochemiluminescent labeled probes for the Aa-ras oncogene.

An assay was conducted and the results are shown in FIG. 9. The PCR was performed as described in FIG. 8 using only biotinylated HRP2 with unlabeled HRP1 (for probes 1T24 and 1CHR). The probes used were: 1T24 and 1CHR containing $P^{32}$ (1T24-P, 1CHR—P) as controls. With the 1T24 and 1CHR containing both $P^{32}$ and ECL label to determine the effects of the ECL label. The samples were washed as earlier with TEMAC. The resultant bead bound $P^{32}$ was analyzed on addition of scintillation cocktail in a scintillation counter. The results were plotted as $p^{32}$ counts per second for each sample probe combination.

Figure 10:
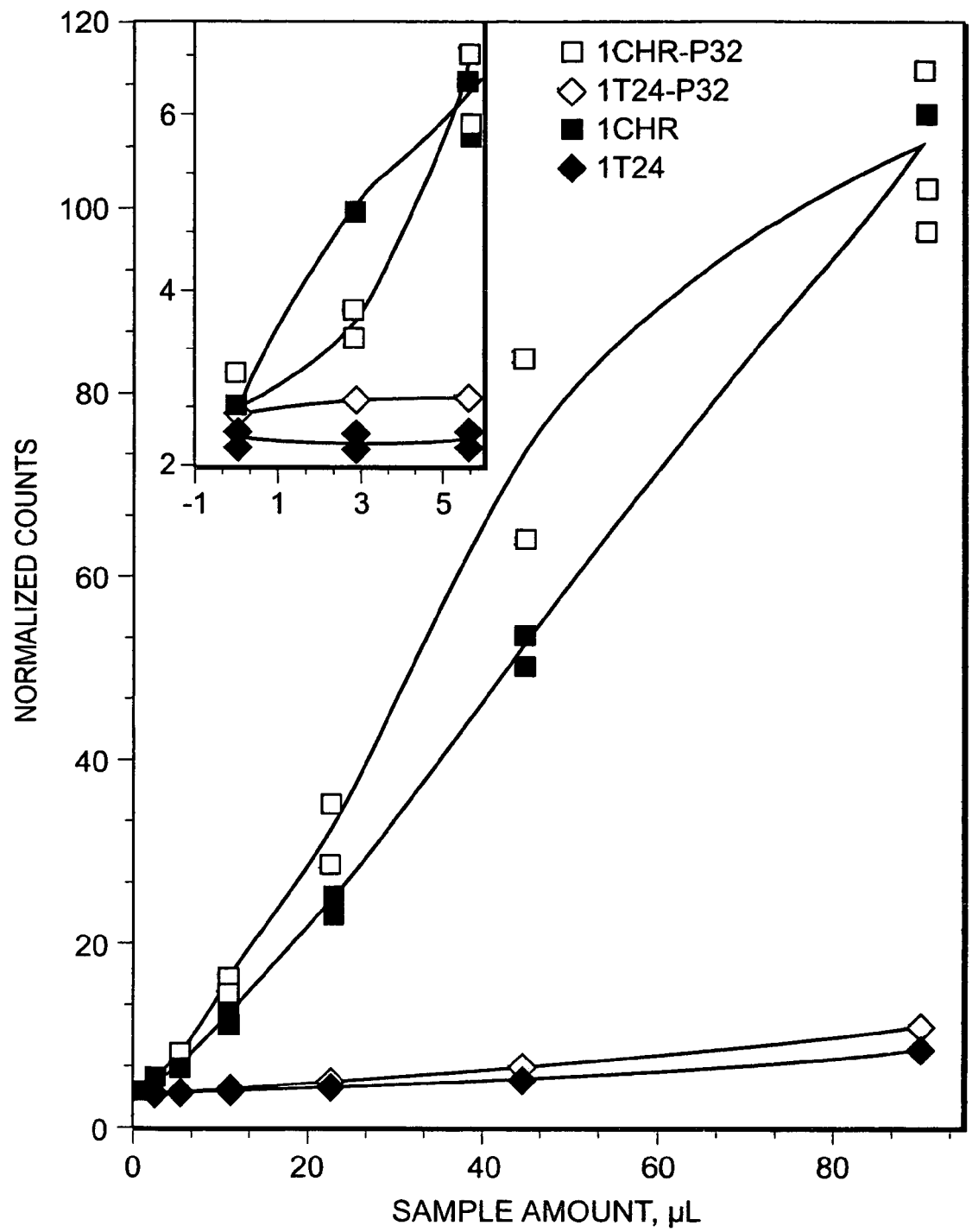
FIG. 10 is a graph showing the determination of the relative value of electrochemiluminescent label in $P^{32}$ electrochemiluminescent label for the determination of point mutations in the Ha-ras oncogene.

An assay was conducted and the results are shown in FIG. 10. The assay was performed as described in FIG. 4. The sample was placental DNA and amplification was performed using biotinylated HRP2 with unlabeled HRP1 (for probes 1T24 and 1CHR). The resultant PCR product was then sampled to give a set of samples containing differing amounts of product. These sets of samples were then hybridized with either probes labeled with $P^{32}$ (1T24-P32 and 1CHR-P32) or ECL label (1T24-ECL and 1CHR-ECL). The results form each studies were then normalized using the average peak value from each label for the 90 µl sample. These normalized figures allow a more effective comparison of signal to background and the comparative response of the two methods. The inset figure illustrates the response at the lower level of the dilution curve. The samples were handled as described earlier. (FIG. 6 and FIG. 8.)

Figure 11:
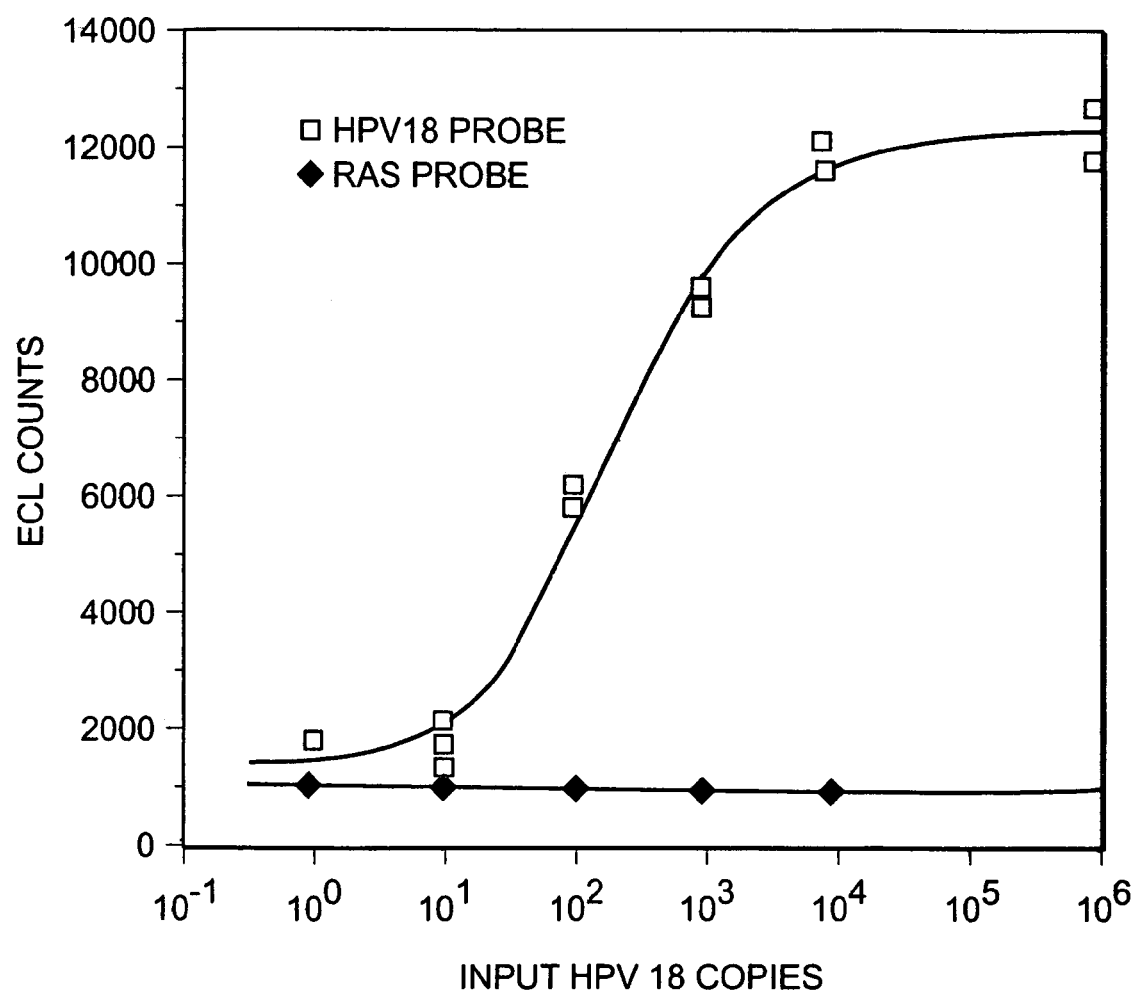
FIG. 11 is a standard curve of the rapid "no wash" hybridization assay for HPV18.

An assay was conducted and the results are shown in FIG. 11. The PCR was performed using biotinylated 2PV18 and unlabeled 1PV18 using HeLa DNA (400 copies per cell) using the PCR format illustrated in FIG. 3. The resultant PCR reaction was then hybridized with the specific probe ECL label-3PV18. The hybridization mixture was then added to streptavidin coated beads and the resultant bead bound ECL label was directly analyzed for ECL using an ECL analyzer as described in FIG. 1. The results were plotted as ECL counts verses HPV18 copies added to the PCR.

EXAMPLES

Instrumentation, Materials, and Methods (1) Instrumentation

A flow-through apparatus, employing three electrodes, as described in FIGS. 1 and 2, was used.
Working Electrode—Au disk, 3 mm diameter
Counter Electrode—Au disk, 3 mm diameter
Reference Electrode—Ag/AgCl
Teflon Gasket (0.15" thick)
Plexiglas Faceplate
Inlet Tubing=0.042" id polypropylene
Aspiration Rates: variable from 0.01 to 5 mL/min
Potentiostat: microprocessor controlled
Luminometer using Hamamatsu R374 PMT (low gain red sensitive tube); PMT Voltage variable 0-1400 V (2) Materials
(a) ECL Label: $Ru(bpy)_3^{2+}$
(b) ECL Buffer: 112 mM $KH_2PO_4$, 88 mM $K_2HPO_4.3H_2O$, 50 µM NaCl, 6.5 mM $NaN_3$, 0.8 µM Tirton X-100, 0.4 mM Tween 20, 100 mM tripropylamine in $H_2O$
(c) ECL Diluent 37.5 mM $KH_2PO_4$, 109.2 mM $K_2HPO_4.3H_2O$, 151.7 mM NaCl, 0.65 mM $NaN_3$, 0.43 mM bovine serum albumin in $H_2O$
(d) $Ru(bpy)_3^{2+}$-NHS: $Ru(2,2'-bipyridyl)_2(4-[3-(1,3-dioxolan-2-yl) propyl]-4'-methyl-2,2'-bipyridine)^{2+}$
(e) Dynal Particles
  (i) Dynal M-450 Dynabeads, 4.5 µm diameter superparamagnetic particles, 30 mg/mL, obtained from Dynal, 45 North Station Plaza, Great Neck, N.Y. 11021
  (ii) Dynal M-280 Dynabeads, 2.8 µM diameter superparamagnetic particles, 10 mg/mL, obtained for Dynal, 45 North Station Plaza, Great Neck, N.Y. 11021

(3) ECL Measurement Cycle (Three Electrode Cell Operation)

The ECL measurement cycle consists of three steps: (1) preconditioning, (2) measuring, and (3) cleaning. The preconditioning step involves the application of a voltage triangle wave of 0.0 V to +2.2 V to −1.0 V to +0.6 V at 2.0 V/sec. The measurement step involves the application of a triangle waveform from +0.6 V to +2.8 V to +2.0 V at 1.0 V/s. The cleaning step involves the application of a voltage square wave from +0.0 V to +3.0 V to −0.5 V to 0.0 V. All voltages are relative to the Ag/AgCl reference electrode.

Example 1

Apparatus and Method for Collection of Microparticles by Gravity

Figure 12:
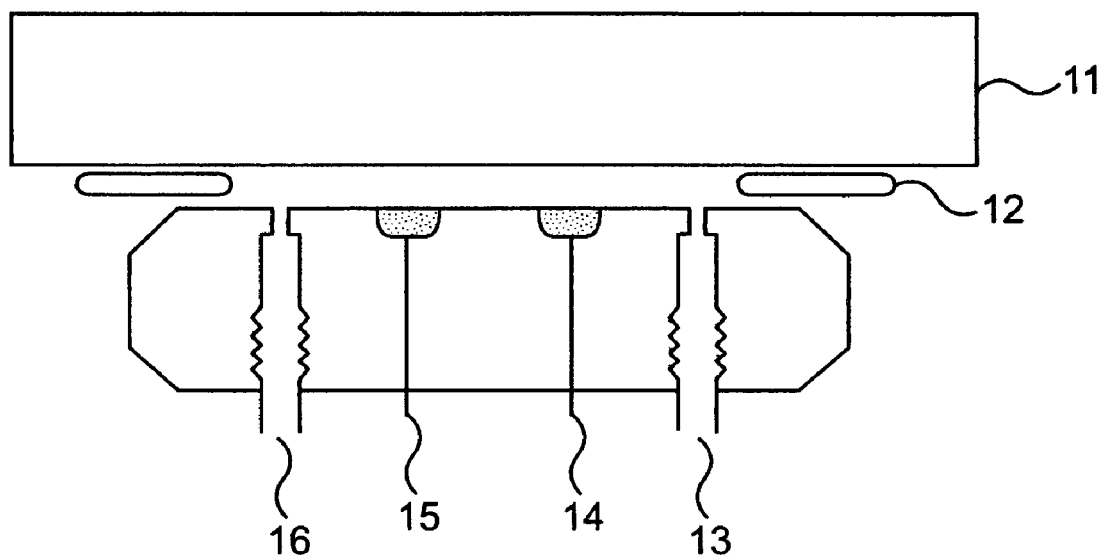
FIG. 12 is a schematic representation of an assay cell used to conduct assays relying upon gravitational force to cause the complex to settle.
Figure 13:
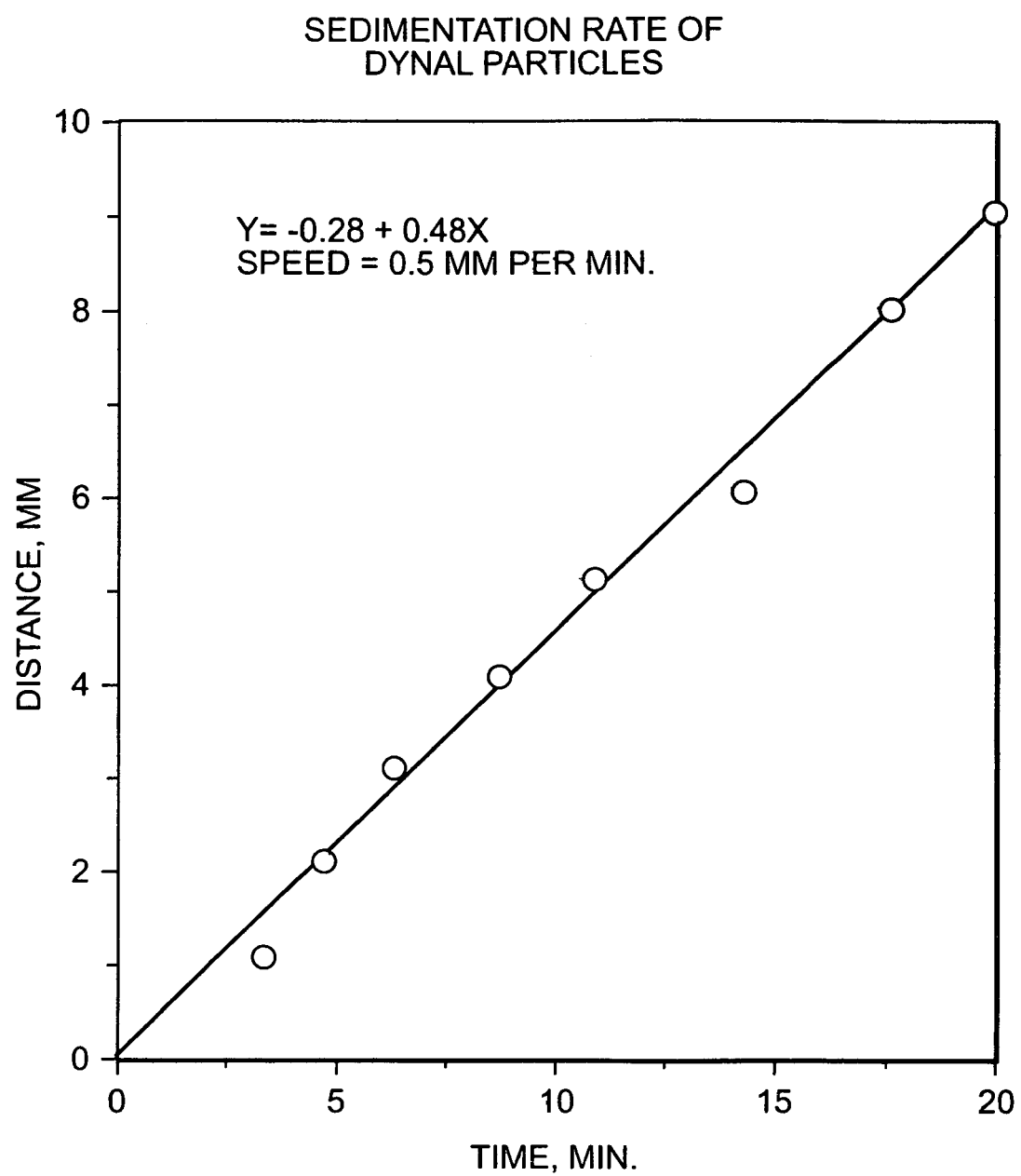
FIG. 13 is a graph showing the distance the complex settles as a function of time under influence of gravity.
Figure 14:
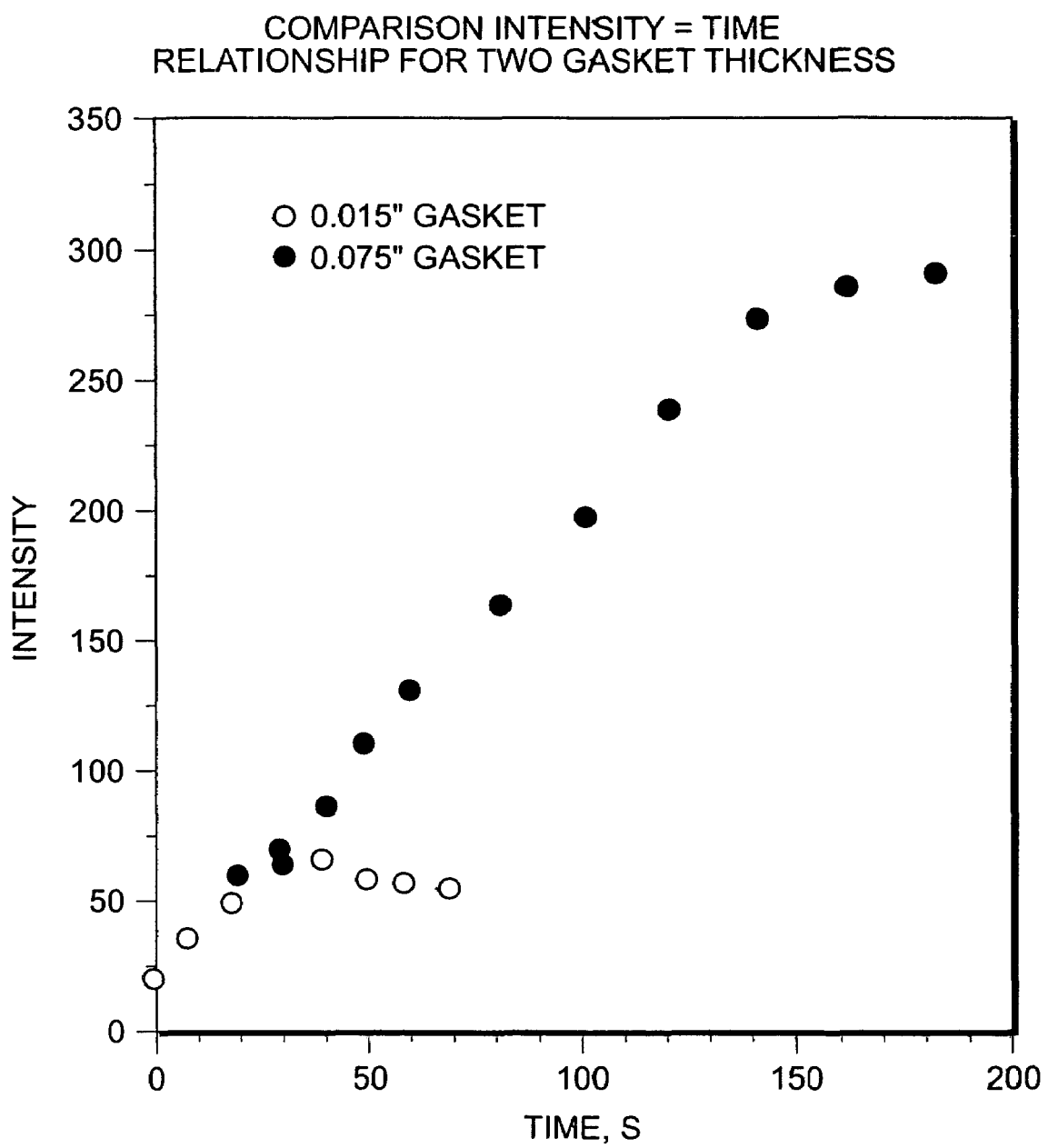
FIG. 14 is a graph showing the intensity of electrochemiluminescence as a function of time in gravity cells having different heights of assay composition over the electrode.
Figure 15:
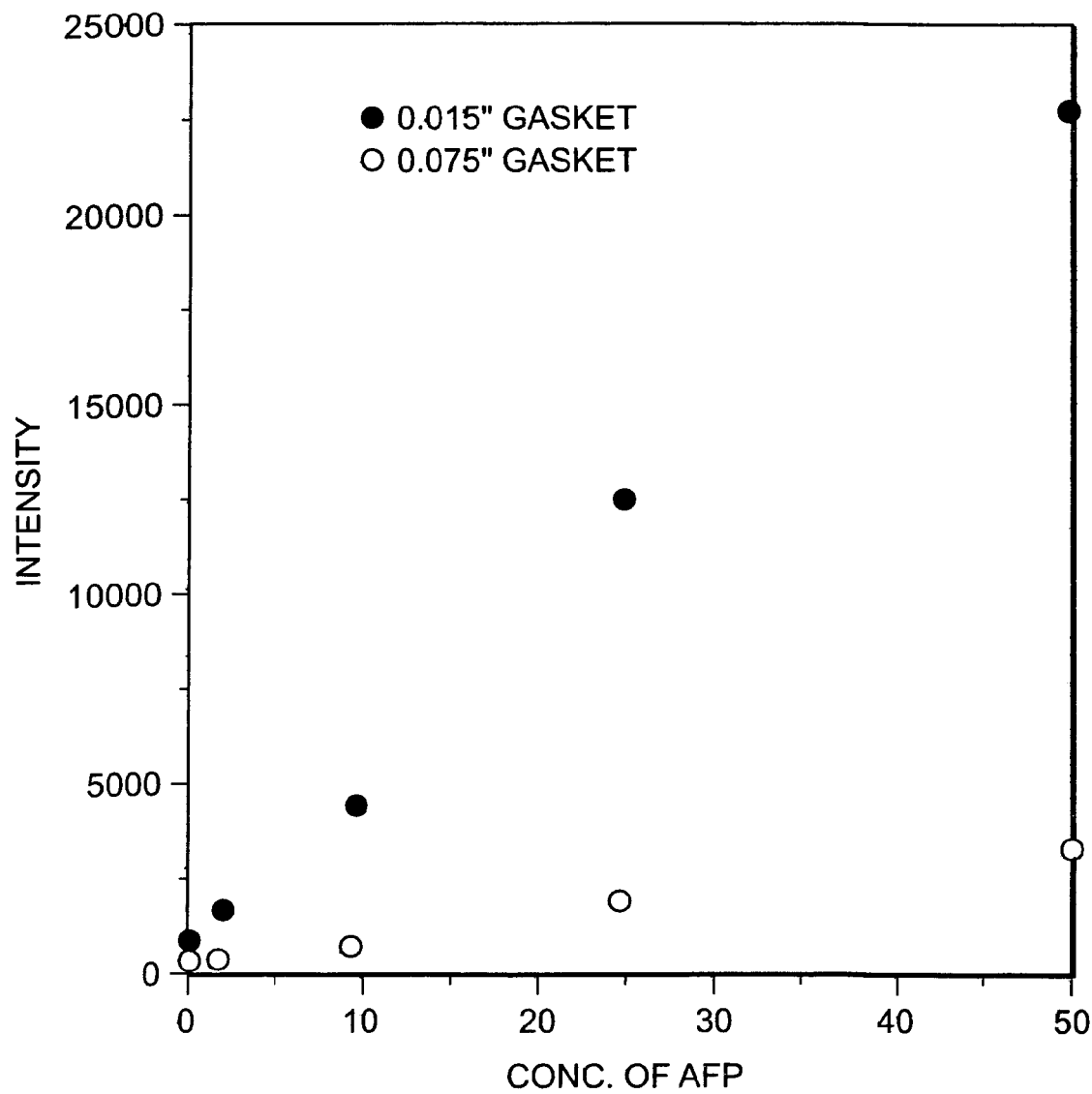
FIG. 15 is a graph showing the intensity of electrochemiluminescence in gravity cells having different heights of assay composition over the electrode surface as measured in an assay for the measurement of alpha fetal protein.

The measurement is conducted in a cell as shown in FIG. 12. References made to FIG. 12 which depict an apparatus for conducting an assay using the force of gravity. The components of the apparatus include a transparent window identified by reference numeral 11, a gasket identified by reference numeral 12, a block which includes an inlet 13, a working electrode 14, a counterelectrode 15 and an outlet port 16. The plane of the cell block is horizontal, i.e. perpendicular to the direction of the earth's gravitational field. Labeled microparticles (Dynal) in an ECL buffer are drawn to the cell by means of a peristaltic pump. The pump is turned off after the particles reach the cell. The microparticles in the cell chamber fall onto the working electrode surface. The rate of fall of microparticles is determined to be approximately constant at 0.5 mm/min over a distance of 10 mm, as shown in FIG. 13. The number of particles to settle is a function of time and rate of fall. The ECL intensity is proportional to the number of particles that settle on the working electrode. The number of particles that reach the surface, and therefore the ECL intensity is limited by the height of fluid sample over the working electrode. FIG. 14 shows the ECL intensity as a function of deposition time for two cells of different gasket thicknesses, 0.015 and 0.075 inches, respectively. Both cells have similar rates of deposition of microparticles but the cell with a thicker gasket gives an maximum reading which is five times larger. The results of an AFP (alpha fetal protein) assay is shown in FIG. 15, comparing the two cells. Again, the cell with the thicker gasket produces five times the ECL signal intensity.

Example 2

ECL Apparatus and Method for Deposition of Microparticles

Magnetic Collection using a Sedimentation Cell.

Figure 16:
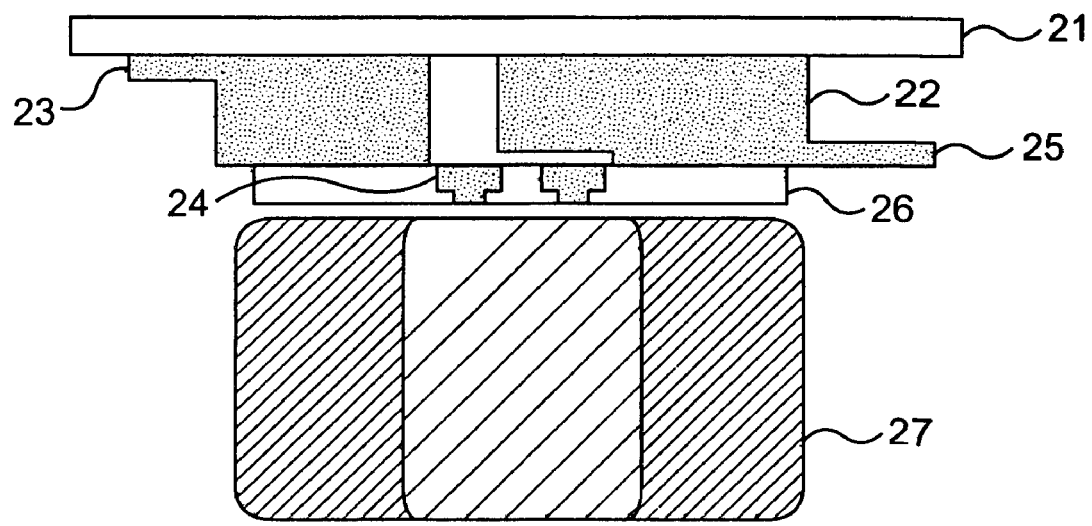
FIG. 16 is a schematic representation of a sedimentation assay cell which employs an electromagnet to cause the complex to settle on the electrode surface.

A cell for conduct of an assay using magnetic force to cause the microparticulate to settle is shown in FIG. 16. Reference numeral 21 refers to a transparent window, reference numeral 22 to a gasket, reference numeral 23 to the inlet in the cell block, reference numeral 24 to the working electrode, reference numeral 25 to the sample outlet, reference numeral 26 to the cell block itself and reference 27 to an electromagnet.

Figure 17:
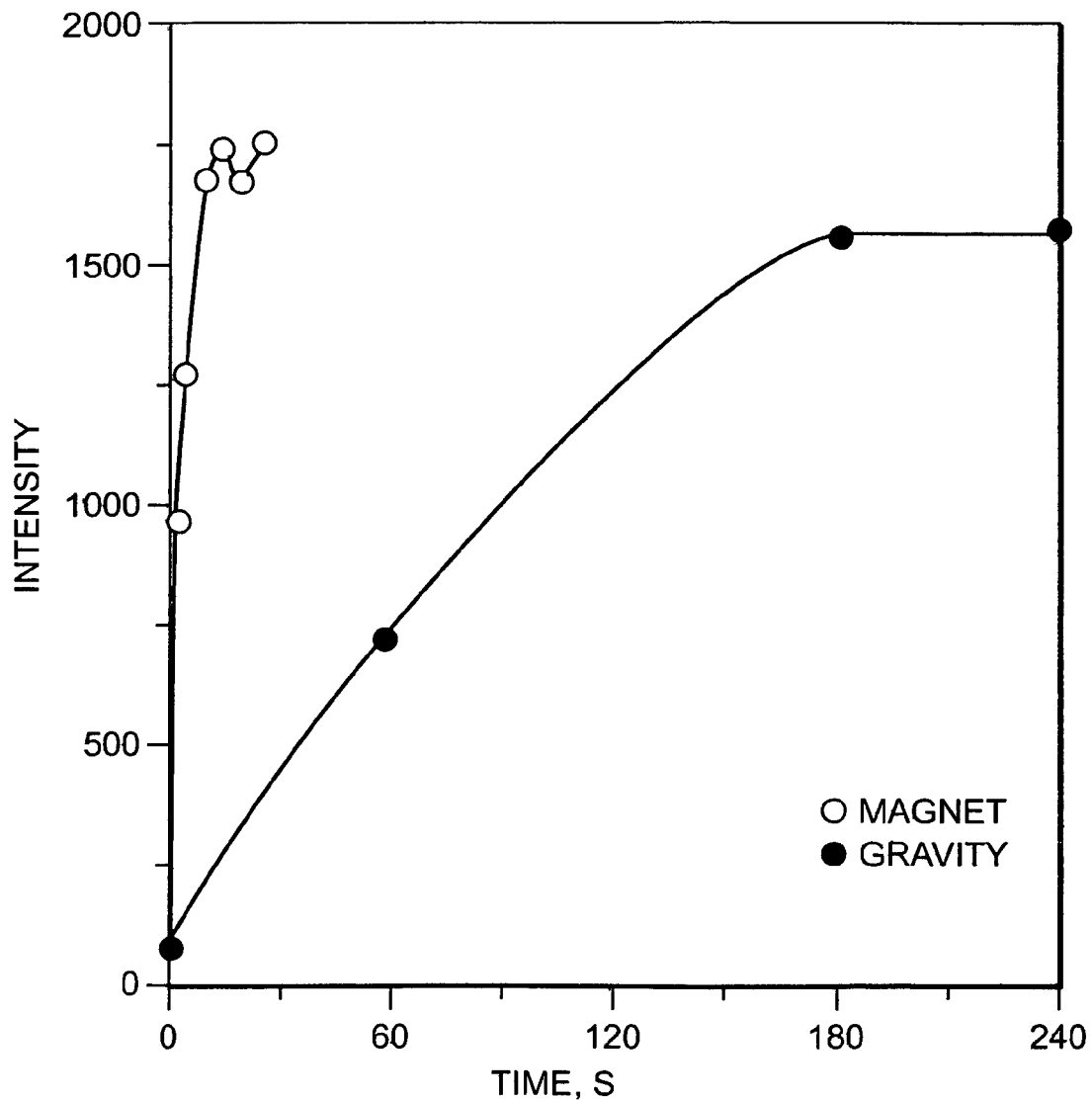
FIG. 17 is a graph showing the relative rates of settling of microparticulate complex under the influence of a magnetic field and of gravity, respectively.

The plane of the cell block is oriented horizontally. Labeled microparticles (Dynal) in ECL buffer are drawn to the cell by means of a peristaltic pump. The pump is turned off after the microparticles reach the cell. The microparticles in the cell chamber are drawn to the working electrode by means of a magnetic field generated using electromagnet 27 operating at 12 volts and 1.5 amps. By application of the electromagnet, the rate of deposition of microparticles is greatly increased over that observed when the microparticles settle solely due to the force of gravity. This is shown in FIG. 17.

Example 3

ECL Apparatus and Method for Deposition of Microparticles

Magnetic Collection using a Collection Cell.

Figure 18:
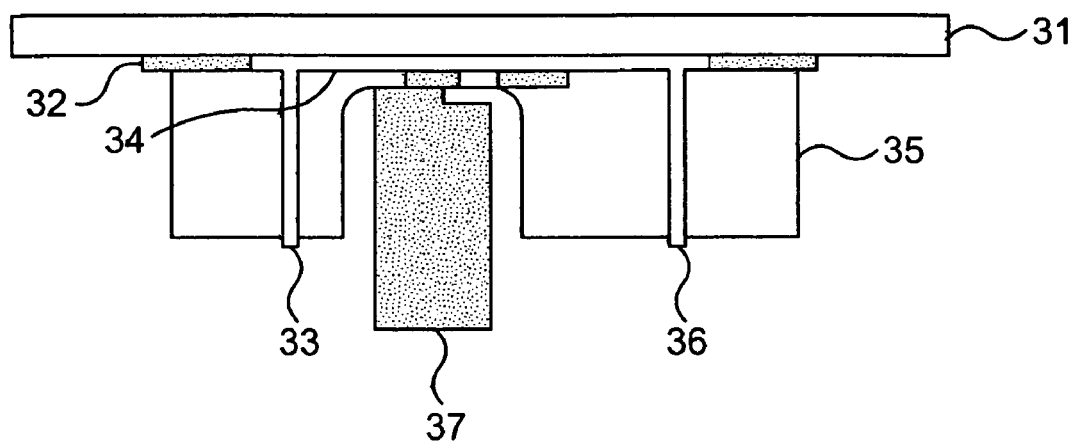
FIG. 18 is a schematic representation of a collection cell including a permanent magnet.

An assay is carried out in a cell as described in FIG. 18. With reference to FIG. 18, reference numeral 31 refers to transparent window, reference numeral 32 to a gasket, reference numeral 33 to an inlet in the cell block, reference numeral 34 to a working electrode, reference numeral 35 to the cell block itself, reference numeral 36 to the sample outlet and reference numeral 37 to a permanent magnet.

Figure 19:
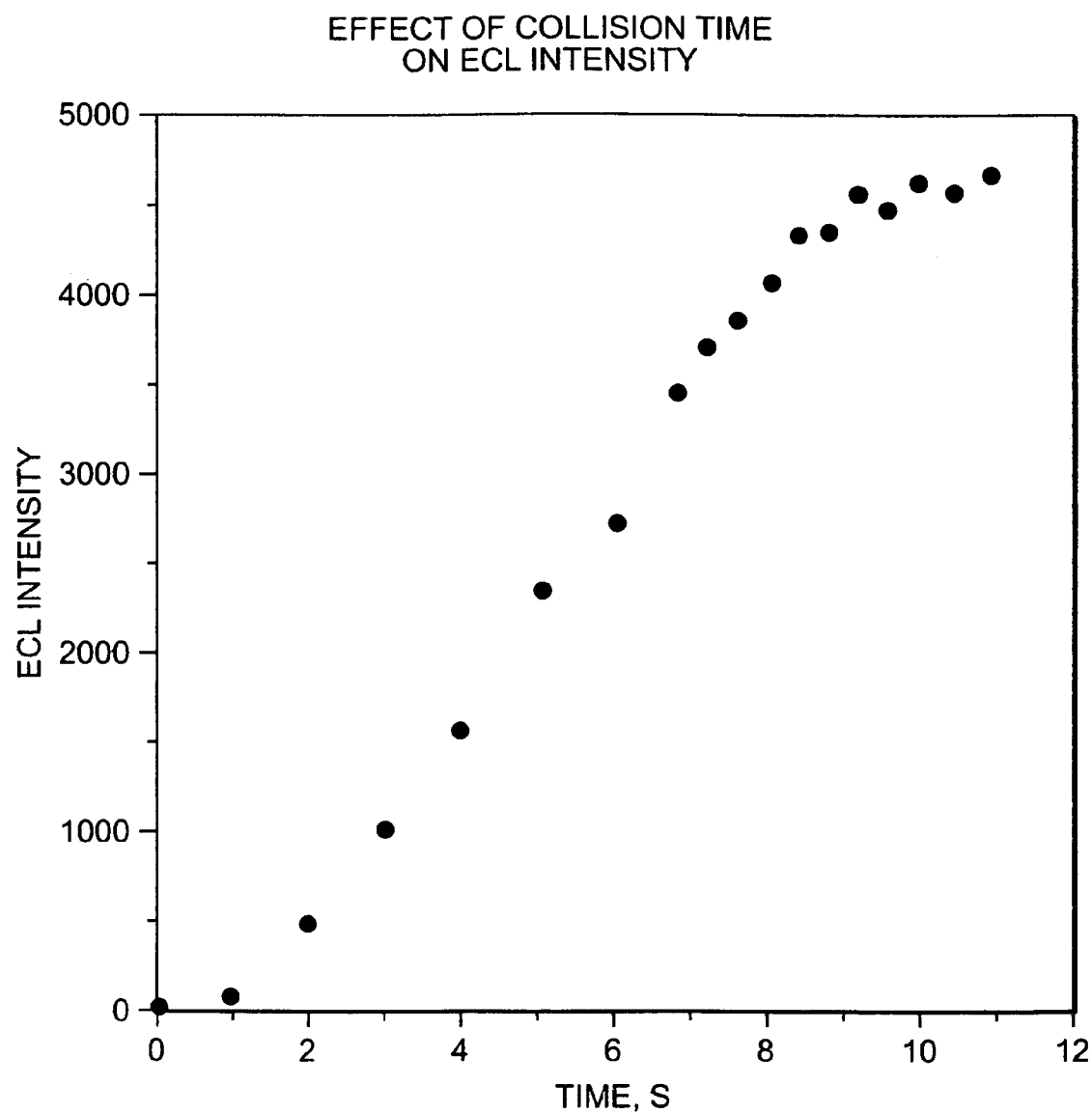
FIG. 19 is a graph showing the increase in ECL intensity as a function of time in assays conducted with the cell of FIG. 18.

The plane of the cell block is oriented horizontally. Labeled microparticles (Dynal) in ECL buffer are drawn to the electrochemical cell by means of a peristaltic pump. Prior to the sample introduction, permanent magnet 34 is positioned immediately below the working electrode/solution interface at a distance of 0.035 inches. As the sample is being drawn to the cell, the microparticles deposit onto an area over the working electrode, as defined by the area of the magnet. The pump is turned off and the magnetic withdrawn after the entire sample is deposited. The longer the collection time, the more particles are deposited. Increasing the concentration of particles on the working electrode results in an increased ECL intensity as shown in FIG. 19.

Example 4

Use of Magnet for Deposition of Microparticles

Magnetic Field Orientation.

Figure 20A:
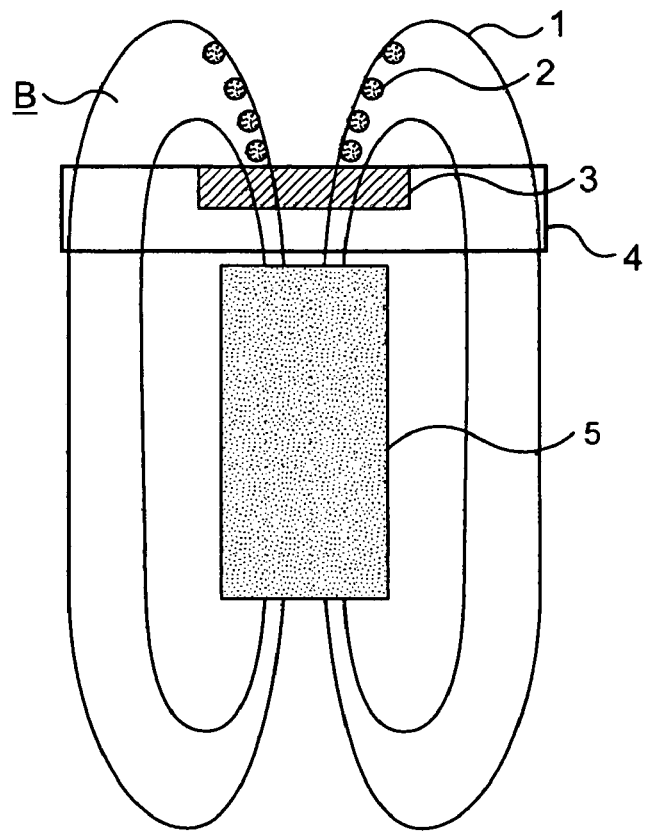
FIG. 20 is a schematic representation of the lines of force in the vicinity of the electrode surface as a function of the orientation of the magnet beneath the electrode surface.
Figure 20B:
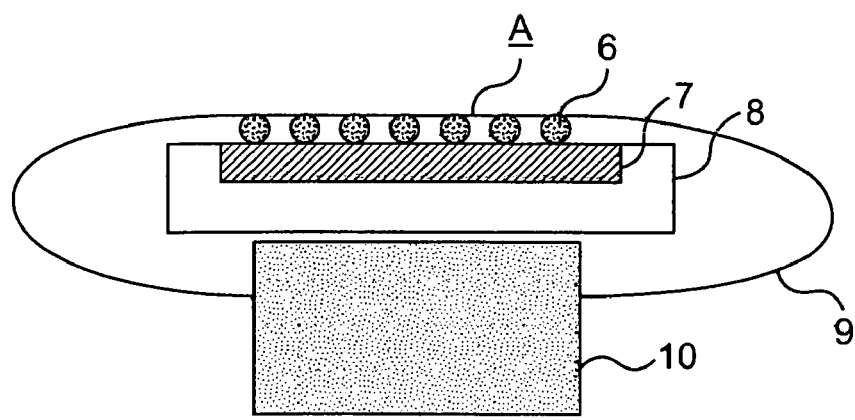
Figure 21:
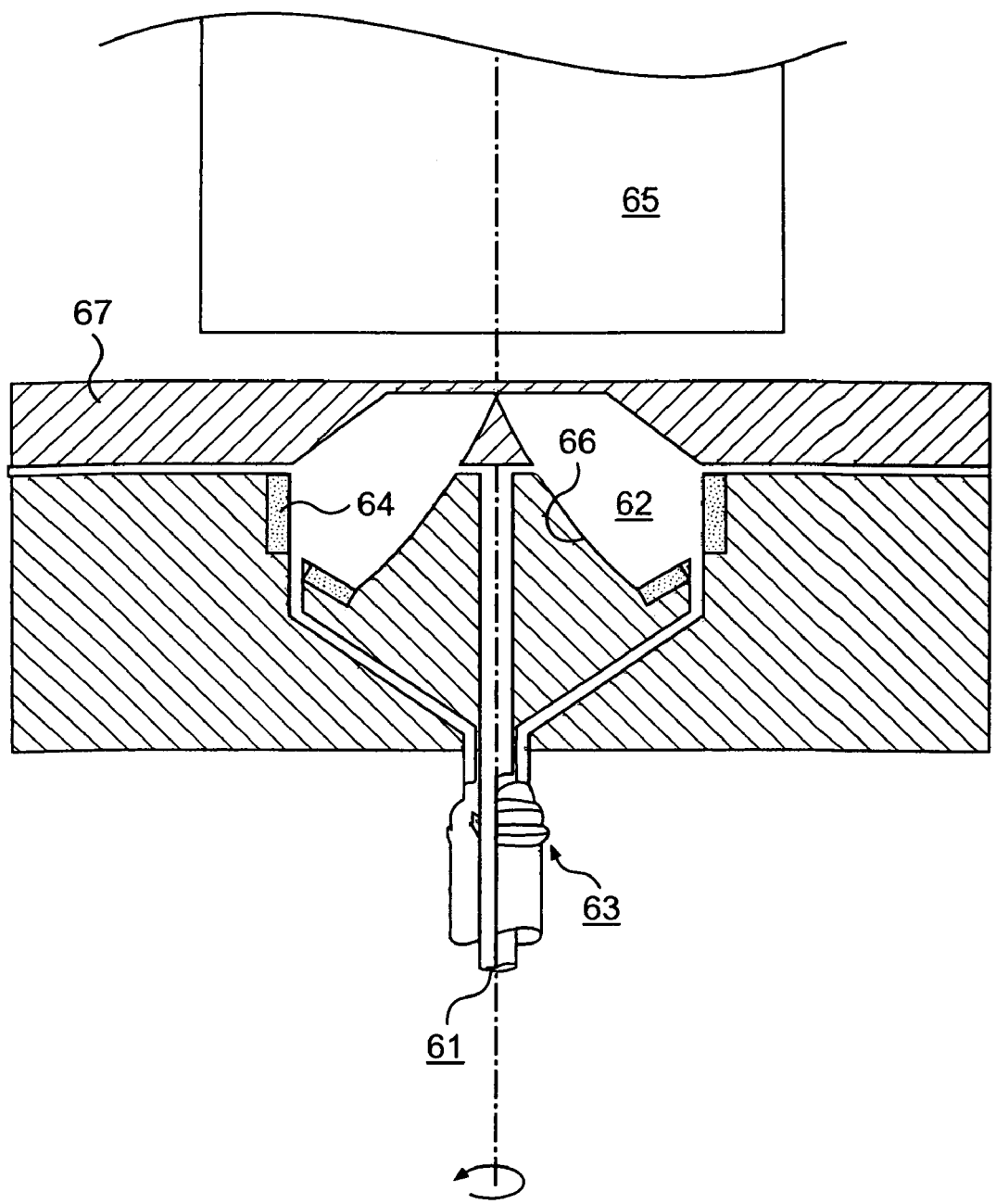
FIG. 21 is a schematic representation of a rotary flow cell wherein the complexes are deposited upon the surface of the electrode by centrifugation.

Microparticles which are attracted to a magnet whether a permanent magnet of or electromagnet, align with the orientation of the magnetic field. FIG. 20 depicts magnetic fields and the resultant particle arrangements which are parallel (A) and perpendicular (B) to the surface of the working electrode, in the vicinity of that surface.

Figure 23:
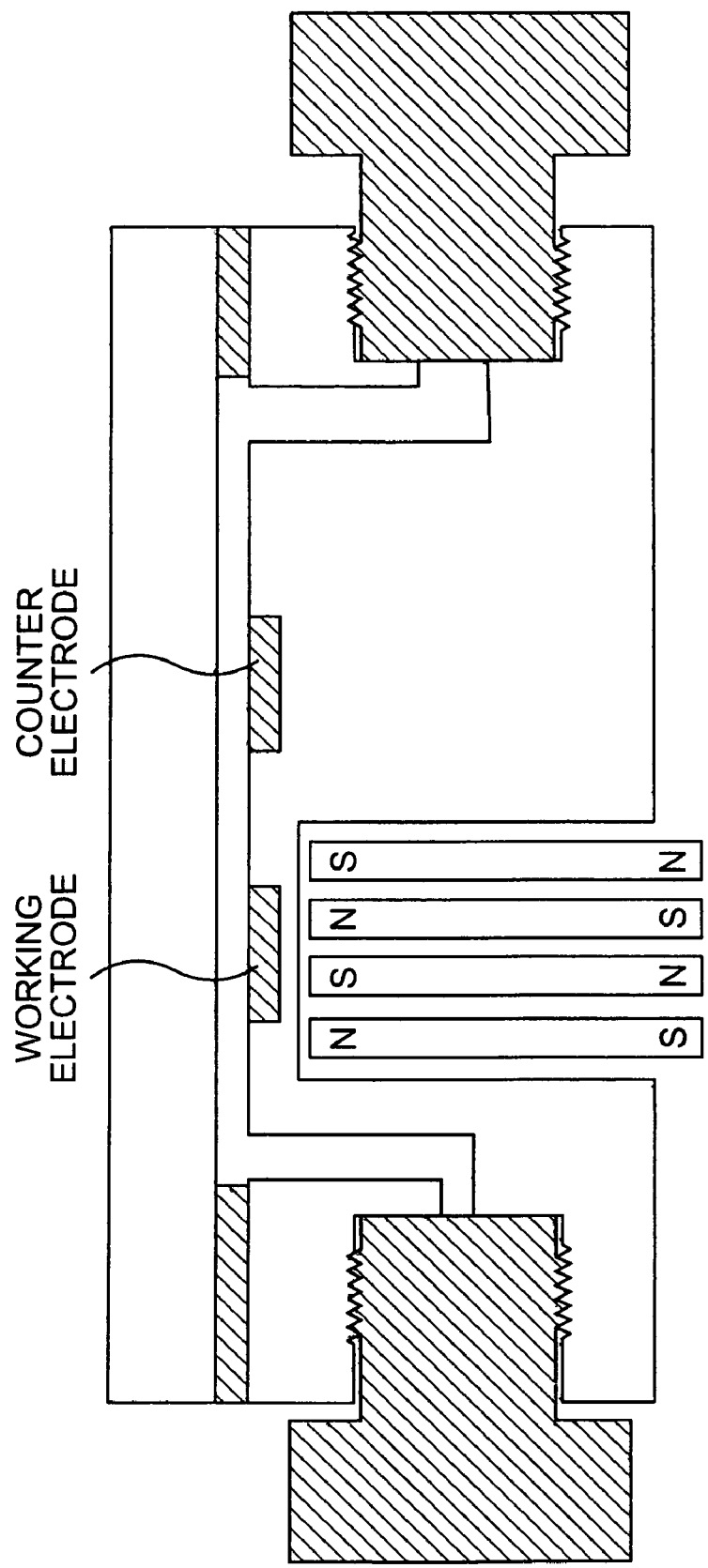
FIG. 23 is a schematic representation of a cell equipped with a magnet system.
Figure 24:
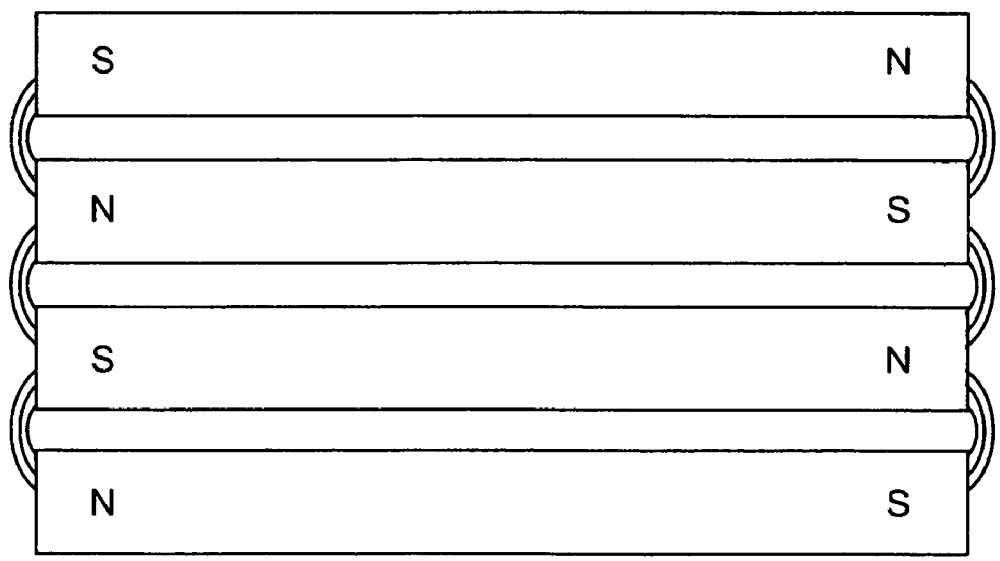
FIG. 24 is a schematic representation of the magnet system of the cell of FIG. 23.

FIGS. 23 and 24 schematically describe a cell which is equipped with a magnet system which advantageously imposes field lines which are largely parallel to the plane of the electrode surface. The magnet system consists of a plurality of individual permanent or electromagnets which are stacked and oriented such that the north and south poles of the magnets alternate in the stack. The individual magnets are separated by air or any non-magnetically responsive material. The arrangement as shown in FIGS. 23 and 24 advantageously applies magnetic lines of force to the region above the working electrode which are nearly horizontal to the plane of the electrode. This induces an orientation of the magnetically responsive particles in which the particles lie upon the surface of the electrode and are supplied readily accessible to the electrochemical energy supplied by the electrode.

The magnet system shown in FIGS. 23 and 24 also is advantageous in that the magnetic field lines do not extend a long distance from the magnet structure. The magnetic field from such a magnet system is not likely, therefore, to induce permanent magnetic behavior on ferromagnetic materials near the electrode apparatus and will not severely affect the operation of a photomultiplier tube near the flow cell apparatus.

Example 5

Particle Collection and Concentration by Filtration

Microparticles which are magnetically responsive, non-magnetically responsive, and of a wide range of densities can advantageously be collected by filtration upon the surface of a membrane filter. In one embodiment of the invention, the particles are pumped through a portion of a filter membrane which has pore sizes which are smaller than the diameter of the particles but preferably are substantially smaller than the particle diameter and at a sufficiently high surface density such that the collection of particles will not cause blockage of the pores. The filter is advantageously largely transparent such that the filter, after collection of the particles, can be placed upon the surface of a working electrode for the purpose of inducing ECL from the particles and measuring the luminescence to measure the quantity of ECL label on the particles.

In another embodiment, the membrane filter having pore sizes as described above is attached or placed upon the surface of an absorbent material such that capillarity or "wicking" will spontaneously draw fluids containing microparticles through the membrane filter without requiring any apparatus to induce the flow of fluid through the filter.

In the preferred embodiment, the membrane filter, having pore sizes as described above, is coated with a thin film of metal or other electronically conductive material such that the surface of the membrane can serve as a working electrode in an ECL apparatus. The conductive films are readily applied to the surface of a membrane by methods commonly used in the fabrication of microelectronic devices, e.g., thermal evaporation or sputtering. Such a filter-electrode is readily mounted in a flow cell such that the flow-path for the fluid is through the filter-electrode. Particles in the stream are trapped by the filter-electrode and are easily washed in-situ providing for a rapid and simple means for performing heterogeneous assays without any external washing apparatus.

Example 6

Particle Collection and Concentration by Centrifugal Method

The rotary flow cell shown in FIG. 20 provides another means to capture the complex on the surface of the working electrode in order to measure luminescence. The assay solution 61 is pumped into cell 62 through rotary seal 63 while a rotational motion is imparted to the cell. The denser particles of the complex are concentrated on the surface of working electrode 64. While the cell is still rotating the solution passes out of the cell. The light output passing through cell window 67 is measured by photomultiplier tube 65. The light output is directed from the vertical working electrode surface 64 reflecting off curved mirror surface 66 located at the center of the cell. The cell is then flushed and cleaned for the next cycle. This may be accomplished with the cell stopped or rotating.

Example 7

Coating of Particles With Labeled Non-specific Protein at Moderate Surface Concentration 30 mg (1 ml) of 4.5 um uncoated magnetically responsive, polystyrene M-450 DYNABEADS (DYNAL, Oslo, Norway) were washed by magnetic seperation with a 150 mM phosphate buffer pH 7.5 solution using 2 ml/wash. 150 μg of Ru(bpy)$_3$$^{2+}$-labeled mouse IgG (Jackson Immunochemicals) in 1 ml of phosphate buffer saline (PBS) with 0.05% thimerasol were added to the particles. This mixture was allowed to incubate overnight at room temperature with rotation. The solution was then magnetically separated from the particles and removed. To block unreacted sites, 1 ml of 3% BSA/PBS with 0.05% sodium azide was added to the particles, and the resultant solution was allowed to incubate 2 hours at room temperature. The particles were washed 5 times (2 ml/wash), and then finally resuspended in 6 ml of the same buffer for storage.

Example 8

Electrochemiluminescent (ECL) Measurement Using Magnetically Responsive Particles Uniform and nonuniform, polymeric and non-polymeric, magnetically responsive particles (Dynal, Oslo, Norway; Polysciences, Warrington, Pa. 18976; Cortex Biochem, San Leandro, Calif. 94577; Aldrich, Milwaukee, Wis. 53201) were coated with labeled proteins as described in Example 7. The coated particles were washed with ECL buffer three times before making 2 mL of a 300 ug/mL suspension. Using a peristaltic pump, 500 ul of the particle suspension was drawn into the flow cell (Example 3). As the particles flowed to the working electrode, they were attracted and concentrated onto the working electrode surface by a magnet. Electrochemiluminescence using the magnetic particles was measured using a Hamamatsu R374 photomultiplier tube centered above the flow cell where particles had concentrated on the working electrode surface. Table I shows ECL photoemission levels obtained from the labeled-protein coated magnetically responsive particles.

TABLE I

ECL Measurements from Different Magnetically Responsive Particles

| Particle Type | Diameter (μm) | Density (g/mL) | Material | ECL Counts |
|---|---|---|---|---|
| Glass | 8.0 | 2.4 | soda lime glass | 2200 |
|  | 2.0 | 2.4 | soda lime glass | 8500 |
| Quartz | 0.3-3.5 | 2.5 | SiO2 | 1150 |
| Gold | 1.0-2.0 | 19.3 | Au | 1100 |

Example 9

Electrochemiluminescent (ECL) Measurement Using Nonmagnetic Particles

Uniform and nonuniform, polymeric and non-polymeric, non-magneticall responsive particles (Aldrich, Milwaukee, Wis. 53201; Duke Scientific, Palo Alto, Calif. 94303) were coated with labeled proteins as described in Example 7. The coated particles were washed with ECL buffer three times before making 2 mL of a 300 ug/mL suspension. Using a peristaltic pump, 500 ul of the particle suspension was drawn into the flow cell. The coated particles were then concentrated onto the working electrode by gravitational means as described in Example 1. Electrochemiluminescence using the nonmagnetic particles was measured with a Hamamatsu R374 photomultiplier tube centered above the flow cell where particles had concentrated on the working electrode surface.

Table II shows ECL photoemission levels obtained from the coated nonmagnetic particles.

Example 10

Preparation of Physically Adsorbed Sheep Anti-Thyroid Stimulating Hormone (TSH) Coated Dynal Particles Reagent I 1 mL of 4.5 μm uncoated magnetic, polystyrene particles with —OH residues on their surface (DYNAL, DYNABEADS M-450, DYNAL A.S. Oslo, Norway) was washed by magnetic separation with a 150 mM sodium carbonate/bicarbonate pH 9.6 solution using 2 mL/wash. 0.5 mg of affinity purified Sheep anti-TSH, HCG scrubbed antibody (CIBA) in 1 mL of the carb/bicarb solution was added to the particles. This mixture was incubated overnight at room temperature with mixing. The solution was then magnetically separated from the particles and removed. 1 mL of 3% BSA/PBS w/0.05% sodium azide was added and incubated 2 hours at room temperature with agitation to block unreacted sites. The particles were washed 5 times (2 mL/wash) then finally resuspended in 1 mL of the same buffer for storage. The final concentration of Bead Reagent I was 3% by weight.

TABLE II

ECL Measurement from non-magnetically responsive Particles by Gravity Collection

| Particle Type | Diameter (μm) | Particle Density (g/mL) | Material | ECL Counts |
|---|---|---|---|---|
| Rhone-Poulenc | 4.0 | 1.5 | Polystyrene Divinyl Benzene/Fe$_3$O$_4$ | 1680 |
|  | 1.5-2.1 | 1.4 | Polystyrene/Fe$_3$O$_4$ | 462 |
| Polysciences | 1.5-2.1 | 2.1 | Polystyrene/FeO$_2$ | 504 |
| Dynal | 4.5 | 1.5 | Polystyrene/Fe$_2$O$_3$ | 4200 |
| Cortex | 1.0-10 | 1.3 | Cellulose/Fe$_3$O$_4$ | 125 |
|  | 1.0-10 | 1.8 | Polyacrolein/Fe$_3$O$_4$ | 125 |
|  | 1.0-25 | 1.2 | Polyacrylamide/Fe$_3$O$_4$ w/charcoal | 125 |
| Nickel | 3.0 | 8.9 | Ni | 125 |

Example 11

Preparation of Ouabain-BSA Conjugate

Reagent II

Activation of Ouabain:

60.4 mg of ouabain octahydrate (Aldrich Cat #14,193-3) in 6 mL of deionized (di) H$_2$O (wrapped in foil) was mixed with 87 mg of sodium metaperiodate (Mallinckrodt Cat #1139) and the mixture was incubated at room temperature for 2 hours, rotating. The reaction was terminated by passing the reaction mixture through Dowex 1×8-50 ion exchange resin (Aldrich Cat #21,740-9) with diH$_2$O. 200 μL 1M sodium phosphate pH 7.2 was added to adjust the pH of the solution to 7.0.

Conjugation of Activated Ouabain to BSA:

50 mg of activated ouabain (4.6 mL) was then added dropwise to 108 mg bovine serum albumin BSA, Miles Fraction V) in 5 mL 0.15M PBS pH 7.8. This is a 40:1 (OUABIN:

BSA) ratio. The reaction was incubated at room temperature for 2 hours, mixing, followed by rapid addition of 30 mg of sodium cyanoborohydride while mixing. Free ouabain and excess sodium cyanoborohydride were removed by dialysis at 4° C. in 0.15M PBS w/0.05% sodium azide pH 7.8. The Ouabain-BSA Conjugate Reagent II was stored at 4° C.

Example 12

Preparation of Physically Adsorbed Ouabain-BSA Coated Dynal Particles

Reagent III 5 mg of 4.5 µm uncoated magnetic, polystyrene particles with —OH residues on their surface (DYNAL, DYNA-BEADS M-450, DYNAL A.S. Oslo, Norway) were washed by magnetic separation with a 150 mM sodium carbonate/bicarbonate pH 9.6 solution using 10 mL/wash. 3 mg of Ouabain-BSA conjugate (Conjugate Reagent II) in 5 mL of the carb/bicarb solution was added to the particles. This mixture was incubated overnight at room temperature while rotating. The solution was then magnetically separated from the particles and removed. 5 mL of 3% BSA/PBS w/0.05% sodium azide was added and incubated 2 hours at room temperature, rotating to block unreacted sites. The particles were washed 5 times (10 mL/wash) then finally resuspended in 1 mL of the same buffer for storage. The final concentration of Bead Reagent III was 3% by weight.

Example 13

Preparation of $Ru(bpy)_3^{2+}$-Labeled Mouse Anti-Digoxin

Reagent IV 1 mg of mouse anti-Digoxin (Cambridge Medical Technologies Cat #200-014 Lot A3575) was labeled with $Ru(bpy)_3^{2+}$. The monoclonal antibody (MAb) anti Digoxin antibody was buffer exchanged using Centricon 30 microconcentrators (Amicon) into 0.15M potassium phosphate buffer, 0.15M NaCl pH 7.8, the final volume being 0.5 mL. Immediately prior to use, 0.5 mg of $Ru(bpy)_3^{2+}$-NHS was dissolved with 125 µL of anhydrous dimethyl sulfoxide (Aldrich). To achieve a 25:1 molar ratio of $Ru(bpy)_3^{2+}$ to protein based on molecular weights of 1057 and 150,000 respectively, 0.18 mg $Ru(bpy)_3^{2+}$-NHS (45 µL) was added to the protein solution while shaking. The reaction tube was incubated in the dark at room temperature, 30 minutes, while shaking. The reaction was terminated by the addition of 25 µL of 1M glycine and incubated for 10 minutes. The reaction mixture was purified by passage through a Sephadex G-25 column (1×20 cm in 0.15M potassium phosphate, 0.15M NaCl with 0.05% sodium azide pH 7.2). The $Ru(bpy)_3^{2+}$-labeled mouse anti-digoxin fractions were collected and pooled. The labeled protein was determined to have 12 labels per protein molecule.

Example 14

Preparation of $Ru(bpy)_3^{2+}$-Labeled Mouse Anti-Thyroid Stimulating Hormone (TSH)

Reagent V 0.5 mg of mouse anti-TSH (CIBA) was labeled with $Ru(bpy)_3^{2+}$. The MAb anti TSH antibody was buffer exchanged using Centricon 30 microconcentrators (Amicon) into 0.15M potassium phosphate buffer, 0.15M NaCl pH 7.8, the final volume being 0.35 mL. Immediately prior to use, 0.5 mg of $Ru(bpy)_3^{2+}$-NHS was dissolved in 75 µL of anhydrous dimethyl sulfoxide (Aldrich). To achieve a 50:1 molar ratio of $Ru(bpy)_3^{2+}$label to protein based on molecular weights of 1057 and 150,000 respectively, 0.176 mg $Ru(bpy)_3^{2+}$-NHS (26.4 µL) was added to the protein solution while shaking. The reaction tube was incubated in the dark at room temperature, 30 minutes, while shaking. The reaction was terminated by the addition of 25 µL of 1M glycine and incubated for 10 minutes. The reaction mixture was purified by passage through a Sephadex G-25 column (1×20 cm in 0.15M potassium phosphate, 0.15M NaCl with 0.05% sodium azide pH 7.2). The $Ru(bpy)_3^{2+}$-labeled mouse anti-TSH fractions were collected and pooled. The labeled protein was determined to have 14 labels per protein. Reagent V.

Example 15

One Step Separation Sandwich Assay for Thyroid Stimulating Hormone (TSH)

100µL serum calibrators (London Diagnostics TSH LumiTAG Kit), 25 µL $Ru(bpy)_3^{2+}$-labeled mouse anti-TSH (Reagent V) in ECL buffer and 25 µL Sheep anti-TSH-DYNAL particles (Reagent I) in ECL buffer were combined and incubated in polypropylene tubes for 15 minutes, at room temperature, with mixing. The particles were then washed by magnetic separation and then resuspending the particles in 500 µL of ECL buffer. This wash procedure was repeated two additional times. Finally, the particles were resuspended in 1 mL of ECL buffer. The electrochemiluminescence (ECL) for each sample was read as described in Example 3. The ECL counts are directly proportional to the concentration of analyte present in the sample (increasing counts as the concentration of analyte increases). Table III demonstrates a representative assay curve.

TABLE III

One-Step Separation Sandwich Assay: Detection of TSH

| TSH Concentration (µIU/mL) | ECL Counts (Duplicate Samples) | |
| --- | --- | --- |
| 0.00 | 1918 | 1885 |
| 0.05 | 2584 | 2530 |
| 0.10 | 3365 | 3288 |
| 0.50 | 8733 | 8652 |
| 2.50 | 35688 | 35347 |
| 10.0 | 125316 | 136994 |
| 25.0 | 300248 | 288272 |
| 50.0 | 549034 | 564948 |

Example 16

One Step Non Separation Sandwich Assay for Thyroid Stimulating Hormone (TSH)

100µL serum calibrators (London Diagnostics TSH LumiTAG Kit), 25 µL $Ru(bpy)_3^{2+}$-labeled mouse anti-TSH (Reagent V) in ECL buffer and 25 µL Sheep anti-TSH-DYNAL 15 particles (Reagent I) in ECL buffer were combined and incubated in polypropylene tubes for 15 minutes, at room temperature, with mixing. Prior to reading results, 1 mL of ECL buffer was added. The electrochemiluminescence (ECL) for each sample was read as described in Example 3.

The ECL counts are directly proportional to the concentration of analyte present in the sample (increasing counts as the concentration of analyte increases). Table IV demonstrates a representative assay curve.

TABLE IV

One-Step Non-Separation Sandwich Assay:
Detection of TSH

| TSH Concentration (µIU/mL) | ECL Counts (Duplicate Samples) | |
|---|---|---|
| 0.00 | 2610 | 2769 |
| 0.05 | 2870 | 2894 |
| 0.10 | 2970 | 2950 |
| 0.50 | 3473 | 3403 |
| 2.50 | 5588 | 5495 |
| 10.0 | 13051 | 13139 |
| 25.0 | 26468 | 27306 |
| 50.0 | 47104 | 48664 |

Example 17

Two Step Separation Competitive Assay for Digoxin

50 µL serum calibrator (TDx Assay, Abbott Labs, Chicago, Ill.) and 25 µL Ru(bpy)$_3$$^{2+}$-labeled mouse anti-Digoxin (Reagent VI) in ECL buffer, were combined and incubated 20 minutes at room temperature with mixing. 25 µL Ouabain-BSA-DYNAL particles (Reagent III) in ECL buffer was added and incubated an additional 20 minutes, at room temperature, with mixing. The particles were then washed by magnetic separation and then resuspending the particles in 500 µL of ECL buffer. This wash procedure was repeated two additional times. Finally, the particles were resuspended in 1 mL of ECL buffer. The electrochemiluminescence (ECL) for each sample was read as described in Example 3. The ECL counts are inversely proportional to the concentration of analyte present in the sample (decreasing counts as the concentration of analyte increases). Table V demonstrates a representative assay curve.

TABLE V

Two-Step Separation Competitive Assay:
Detection of Digoxin

| Digoxin Concentration (ng/mL) | ECL Counts (Duplicate Samples) | |
|---|---|---|
| 0.0 | 22031 | 21154 |
| 0.5 | 13367 | 13638 |
| 1.0 | 9506 | 9607 |
| 2.0 | 5244 | 5129 |
| 3.0 | 2959 | 2994 |
| 5.0 | 1581 | 1631 |

Example 18

Two Step Non Separation Competitive Assay for Digoxin

50 µL serum calibrator (TDx Assay, Abbott Labs, Chicago, Ill.) and 25 µL Ru(bpy)$_3$$^{2+}$-labeled mouse anti-Digoxin (Reagent VI) in ECL buffer, were combined and incubated 20 minutes at room temperature with mixing. 25 µL Ouabain-BSA-DYNAL particles (Reagent III) in ECL buffer was added and incubated an additional 20 minutes, at room temperature, with mixing. Prior to reading, the particles were resuspended in 1 mL of ECL buffer. The electrochemiluminescence (ECL) for each sample was read as described in Example 3. The ECL counts are inversely proportional to the concentration of analyte present in the sample (decreasing counts as the concentration of analyte increases). Table VI demonstrates a representative assay curve.

TABLE VI

Two-Step Non-Separation Competitive Assay:
Detection of Digoxin

| Digoxin Concentration (ng/mL) | ECL Counts (Duplicate Samples) | |
|---|---|---|
| 0.0 | 42051 | 39643 |
| 0.5 | 28721 | 28074 |
| 1.0 | 22190 | 21364 |
| 2.0 | 14660 | 14542 |
| 3.0 | 11315 | 11893 |
| 5.0 | 9161 | 8945 |

Example 19

Two Step Non Separation Competitive Assay for Digoxin Using a Read Cycle With Additional Washing of Final Reaction Sample on the Electrode 50 µL serum calibrator (TDx Assay, Abbott Labs, Chicago, Ill.) and 25 µL Ru(bpy)$_3$$^{2+}$-labeled mouse anti-Digoxin (Reagent VI) in ECL buffer, were combined and incubated 20 minutes at room temperature with mixing. 25 µL Ouabain-BSA-DYNAL particles (Reagent III) in ECL buffer was added and incubated an additional 20 minutes, at room temperature, with mixing. Prior to reading, the particles were resuspended in 1 mL of ECL buffer. The electrochemiluminescence (ECL) for each sample was read as described in Example 3. The ECL counts are inversely proportional to the concentration of analyte present in the sample (decreasing counts as the concentration of analyte increases). Table VII demonstrates a representative assay curve.

TABLE VII

Two-Step Separation Competitive Assay:
Detection of Digoxin

| Digoxin Concentration (ng/mL) | ECL Counts (Duplicate Samples) | |
|---|---|---|
| 0.0 | 42613 | 35309 |
| 0.5 | 24211 | 24168 |
| 1.0 | 17561 | 17206 |
| 2.0 | 10491 | 9909 |
| 3.0 | 6712 | 7145 |
| 5.0 | 4680 | 4603 |

Example 20

Oligonucleotide Synthesis

The oligonucleotides were made on an Applied Biosystems automated oligonucleotide synthesizer using the β-cyanoethyl phosphoramidite (1). Oligonucleotide amino modifications to the 5' end occurred at the last coupling step, and at the 3' end by using a modified solid phase (controlled pore glass). Clontech (San Diego Calif.) supplied the amino modifiers. The resulting 5' modified oligonucleotides all contain a six carbon spacer arm to the amino group designated (C6, NH2). The 3' modified oligonucleotides all contain a three carbon spacer to the amino group.

Oligonucleotides constructed, their modifications and utility are described below.

Oligonucleotides for the HPV study were directed to the E6 region as previously described (2).

The oligonucleotide sequences were as follows:

```
HPV 16;                                       (SEQ ID NO: 1)
1PV16 5' (C6, NH2) TTAGTGAGTATAGACATTATTGTTATAGTT;

(SEQ ID NO: 2)
2PV16 5' (C6, NH2) CAGTTAATACACCTAATTAACAAATCACAC;

(SEQ ID NO: 3)
3PV16 5' (C6, NH2) ACAACATTAGAACAGCAATACAACAAACCG;

HPV18;                                        (SEQ ID NO: 4)
1PV18 5' (C6, NH2) TTAGAGAATTAAGACATTATTCAGACT;

(SEQ ID NO: 5)
2PV18 5' (C6, NH2) CACCGCAGGCACCTTATTAATAAATTGTAT;

(SEQ ID NO: 6)
3PV18 5' (C6, NH2) GACACATTGGAAAAACTAACTAACACTGGG.
```

These oligonucleotides enable the PCR generation of various fragments; 3PV16 or 3PV18 with 2PV16 or 2PV18 respectively form a 62bp fragment; 1PV16 with 2PV16 form a 100bp fragment; 1PV18 with 2PV18 form a 103bp fragment. It will be appreciated that the 3PV16 and 3PV18 oligonucleotides can also be used as probes hybridizing to the products from the PCR reaction of 1PV16 with 2PV16 and 1PV18 with 2PV18, hybridizing to the strand produced by the oligonucleotides 2PV16 and 2PV18 within the PCR.

Oligonucleotides for the Ha-ras point mutation assays were as follows:

```
                                              (SEQ ID NO: 7)
HRP1 5' (C6, NH2) GCGATGACGGAATATAAGCTGGTGGTGGTG;

(SEQ ID NO: 8)
HRP2 5' (C6, NH2) TTCTGGAT-
                  CAGCTGGATGGTCAGCGCACTC.
```

These two oligonucleotide primers direct the PCR synthesis of an 80bp fragment. The sequences of the probes used for this point mutation study were as follows:

```
                                              (SEQ ID NO: 9)
1T24 5' (C6, NH2) GGCGCCGTCGGTGTGGGCAA;

(SEQ ID NO: 10)
1CHR 5' (C6, NH2) GGCGCCG-
                  GCGGTGTGGGCAA;

(SEQ ID NO: 11)
2T24 5' (C6, NH2) TTGCCCA-
                  CACCGACGGCGCC;

(SEQ ID NO: 12)
2CHR 5' (C6, NH2) TTGCCCA-
                  CACCGCCGGCGCC.
```

Aside from these sequences we also synthesized the above 1CHR and 2T24 sequences without the 5' amino modification but with a 3' amino group. These 3' amino modified oligonucleotides were labeled with the ECL label and used in hybridizations. The site of the mutation/mismatch is indicated by the nucleotide in bold. The probes 1T24 and 1CHR hybridize to the strand produced by oligonucleotide HRP2 within the PCR. The probes 2T24 and 2CHR hybridize to the strand produced by oligonucleotide HRP1 within the PCR.

Oligonucleotides JK8 and JK8C for coupling to particles:

```
JK8                                          (SEQ ID NO: 13)
5' (C6, NH2) GTCCAATC-
CATCTTGGCTTGTC-
GAAGTCTGA;

JK8C                                         (SEQ ID NO: 14)
5' (C6, NH2) TCAGACTTC-
GACAACCCAAGATGGATTGGAC.
```

These two sequences are derived from aequorin sequences and are complementary to each other.

```
                                              (SEQ ID NO: 15)
JK7 5'TCAGACTTCGACAA (NH2) CCCAAGATGGATTGGA.
```

This oligonucleotide was amino modified using an amino modifier from Clontech (San Diego Calif.) which allows amino modifications within the sequence. JK7 was labeled using the Ru(bpy)$_3^{2+}$-label.

Oligonucleotide probe for aequorin RNA generated by in vitro transcription:

```
                                              (SEQ ID NO: 16)
T35 5' (NH2) GATTTTTCCATTGTGGTTGACATCAAGGAA;
``` this oligo was labeled with both biotin and Ru(bpy)$_3^{2+}$-label.

For the detection of *Escherichia coli* DNA we synthesized oligonucleotides specific for the Trp E/D region of the genome (3) as follows:

```
TRP.CO3                                       (SEQ ID NO: 17)
5' (C6, NH2) GCCACG-
CAAGCGGGTGAGGAGTTCC
(NH2);
``` this sequence was labeled with Ru(bpy)$_3^{2+}$-label and

```
                                              (SEQ ID NO: 18)
TRP.CO4 5' (C6, NH2) GTCCGAGGCAAATGCCAATAATGG
``` was labeled with biotin as described below.

Example 21

Labeling Oligonucleotides

All the synthetic oligonucleotides were purified to remove any contaminating amino groups by gel filtration on a Biogel P6 (BioRad Labs) column. Biotin was introduced via the 5'-amino group of the PCR primers using NHS-biotin (Clontech, San Diego, Calif.) (4). Ru(bpy)$_3^{2+}$-NHS was introduced via the amino group of the modified oligonucleotides as follows. The oligonucleotides (0.1 μmole) in 100 μl of PBS (pH 7.4) were reacted with 5 μmole of Ru(bpy)$_3^{2+}$-label dissolved in DMSO overnight at room temperature in the dark. Oligonucleotides were recovered from these labeling reactions by ethanol precipitation. Recent studies have demonstrated the ability to effectively label (>80%) using 0.5 μmole of the Ru(bpy)$_3^{2+}$-label (data not shown).

The labeled oligonucleotides were further purified by HPLC on a reverse phase Vydac C-18 semiprep column with mobile phases of A) 100 mM tetraethyl-ammonium acetate pH 7.0 and B) 50% A and 50% acetonitrile, running the gradient from 20% to 40% of B.

Probes 1CHR and 1T24 were also labeled with $^{32}$P using T4 polynucleotide kinase using established methods generating probes with a specific activity of 77,000 cpm/ng (5).

Example 22

Preparation of Nucleic Acid Magnetic Particles

Dynal M 450 particles were activated with 2-fluoro-1-methylpyridinium toluene-4-sulfonate using standard procedures (6). These activated particles were then reacted with oligonucleotides JK8 and JK8C. To 100 mg of activated Dynal particles were added 33 nmoles of oligonucleotide in 650 µl of 0.1M NaHCO$_3$ followed by incubation for 3 hours with mixing. The particles were blocked by the addition of ethanolamine (4 mL, 0.1M). The coupled particles were mixed with 0.5 mg/mL single stranded salmon sperm DNA in ECL buffer, washed 4-5 times into ECL buffer and resuspended at 10 mg/mL in ECL buffer containing 100 µg/mL single stranded salmon sperm DNA.

Example 23

Preparation of Streptavidin Magnetic Particles I

Dynal M 450 particles were activated with 2-fluoro-1-methylpyridinium toluene-4-sulfonate using standard procedures (6). The activated particles were then reacted with streptavidin (Sigma Ltd). Activated particles (50 mg) were washed with 0.1M NaHCO$_3$ followed by the addition of streptavidin (1.5 mg) and reacted overnight. The particles were blocked by the addition of ethanolamine (4 mL, 0.1M). The coupled particles were mixed with 0.5 mg/mL single stranded salmon sperm DNA in ECL buffer, washed 4-5 times into ECL buffer and resuspended at 10 mg/mL in ECL buffer containing 100 g/mL single stranded salmon sperm DNA. The streptavidin particles from Dynal M-280 also proved valuable but gave lower signals with the current assay sequence. For immunoassay applications particles were blocked with BSA after antigen or antibody coupling using the buffers used for passive coating.

Example 24

Preparation of Streptavidin Magnetic Particles II

To 15 mg of BSA (in 2-3 mL PBS), 105 ul of dimethylsulfoxide containing 50 mg/mL of biotin-x-NHS (Clontech, San Diego, Calif. 5002-1) was added followed by mixing and incubation at room temperature for 30 minutes. The reaction was stopped by adding 30 ul of 1M glycine and incubation at room temperature for 10 minutes. The reaction mix was purified by gel filtration chromatography (Biorad, Bio-Gel P6,). This biotin-BSA was filtered using 0.2 um syringe. 5 mg biotin-BSA in 10 mL of 0.2 M sodium carbonate/bicarbonate buffer pH 9.6 (carbonate/bicarbonate) buffer was added to 300 mg of Dynabeads washed with carbonate/bicarbonate (Dynal 14002). This mixture was Vortexed, and incubated overnight at room temperature with mixing. These particles were magnetically separated followed by the addition of 10 mL ECL diluent and 100 ul tRNA (10 mg/mL). This mixture was incubated for 3-4 hours at room temperature with mixing.

These particles were washed once with 10 mL of ECL diluent and resuspended in 10 mL of ECL diluent and 100 ul tRNA (10 mg/mL). This mixture was mixed and incubated at 2-6° C. overnight to stabilize proteins on particles. The particles were magnetically separated and suspended in 10 mL of PBS containing 15 mg of streptavidin (Scripps S1214) followed by mixing for one hour. The particles were washed 4 times in 10 mL ECL diluent, with 5 minutes mixing for each wash. The particles were finally resuspended in 29.7 mL of ECL diluent and 300 ul tRNA (10 mg/mL) to a final concentration of 10 mg/ mL particles +100 ug/mL tRNA.

Example 25

Detection of Immobilized DNA on Particles by Hybridization with ECL DNA Probes

The ability to detect ECL after hybridization to particles was demonstrated by the hybridization of particles coupled to JK8 and JK8C with Ru(bpy)$_3^{2+}$-label oligonucleotide JK7. Individual lots of particles (300 µg) in ECL buffer were mixed with 50 µl of ECL buffer containing 12.5, 6.3, 3.01, and 1.5 fmoles of labeled JK7. These mixtures were hybridized for 4 hours at 52° C. followed by washing with 1 mL of ECL buffer and resuspension in 830 µl of ECL buffer. These samples were analyzed as described in Example 1. The probe JK7 is complementary to the JK8 sequence and not complementary to JK8C sequence.

TABLE VIII

| Particles | Probe amount (fmoles) | ECL counts |
|---|---|---|
| JK8 | 12.5 | 5085 |
|  | 6.3 | 3035 |
|  | 3.01 | 1345 |
|  | 1.5 | 657 |
| JK8C | 12.5 | 451 |
|  | 6.3 | 345 |
|  | 3.01 | 256 |
|  | 1.5 | 212 |

The results shown in Table VIII demonstrate the ability to detect by specific hybridization the presence of specific sequences directly immobilized on the surface of particles by ECL.

Example 26

RNA Assay Based on Bead Bound ECL

Dynal M450 particles were coated with antibody specific for RNA/DNA antibodies (7) following standard procedures (Example 10). Specific RNA species were generated using plasmids derived from our cloned aequorin gene (8). In brief, the plasmid pA5' was cut with EcoRI purified and subjected to in vitro transcription using T3 RNA polymerase generating T3-RI RNA (negative RNA). Also plasmid pA5' was cut with BamHI purified and subjected to in vitro transcription using T7 RNA polymerase generating T7-Bam RNA (positive RNA). These two RNA species thus represent two complementary RNA species. These RNA species were purified by extraction with an equal volume of phenol:chloroform (50:50) followed by chloroform extraction and precipitation of the supernatant using 2.5 vols of ethanol. The amount of RNA was determined using gel electrophoresis and spectrophotometry. These methods are well established and known to those skilled in the art (9).

Streptavidin was labeled with Ru(bpy)$_3^{2+}$-label using established methods using a 25:1 molar excess of Ru(bpy)$_3^{2+}$-label over streptavidin (Example 13). This labeled streptavidin was purified using an iminobiotin column following established methods (10). The streptavidin was estimated to contain 10 Ru(bpy)$_3^{2+}$-labels per streptavidin tetramer. This labeled streptavidin was then complexed with biotinylated T35, this was achieved using a one to one mix of oligonucleotide to labeled streptavidin. Specifically 20 pmoles of each were mixed in a final volume of 15 µl of ECL buffer and incubated over night at 4° C. to form the labeled streptavidin-oligonucleotide (SA-T35) complex. The samples of positive and negative RNA (long) were hybridized to 2 µl of the SA-T35 complex (one step assay) or 25 ng of the biotinylated T35 (two step assay). Samples were made up to 50 µl and hybridized for 3 hours at 50° C. followed by the addition of 200 µg of anti DNA/RNA antibody coated particles in 20 µl of PBS 0.1% BSA. This mixture was mixed at room temperature for 1 hour followed by two washes in ECL buffer. Samples from the hybridization with the SA-T35 complex were resuspended in 530 µl of ECL buffer and analyzed as described in Example 1. Those samples from the hybridization with biotinylated T35 alone were then incubated with 50 pmoles of labeled streptavidin and incubated for 1 hr with mixing followed by two washes in ECL buffer. Samples from the hybridization were resuspended in 530 µl of ECL buffer and analyzed as described in Example 1. The results are presented in Table IX.

TABLE IX

| ASSAY | RNA | ECL COUNTS (average) |
|---|---|---|
| One Step | Positive | 815 |
| | Negative | 91 |
| Two Step | Positive | 1123 |
| | Negative | 194 |

Example 27

Polymerase Chain Reactions

Polymerase chain reaction's were performed essentially as described (11, 12, 13). Reactions were typically of 100 µl unless otherwise stated. PCR carried out in the asymmetric mode directed incorporation of the Ru(bpy)$_3^{2+}$-label, using 5 pmoles of the biotinylated oligonucleotide and 50 pmoles of Ru(bpy)$_3^{2+}$-label oligonucleotide. We ran the assay for the Ha-ras point mutation under identical conditions but without the Ru(bpy)$_3^{2+}$-labeled oligonucleotide. Also, we ran the non-separation HPV assay asymmetrically but making use of a ten fold excess of the biotinylated oligonucleotide typically 40 pmoles. The thermocycler conditions were as follows, for the direct incorporation HPV 18 and 16 assay, the profile was 93° C. 1 sec, 50° C. 1 sec, 60° C. 2 min; for the Ha-ras point mutation assay 93° C. 1 sec, 69° C. 2 min; for the non-separation HPV assay 93° C. 10 sec, 50° C. 30 sec, 60° C. 2 min. The cycle numbers for these PCR runs were from 30 to 40 depending on the assay and the required degree of sensitivity.

Example 28

DNA-Probe Assay Format I. Detection and Quantitation of HumanPapilloma Virus PCR Products by Enzymatic Incorporation.

Following PCR using direct incorporation of the Ru(bpy)$_3^{2+}$-label oligonucleotide, the whole reaction mixture (90-100 µl) was added to 600 µg of streptavidin coupled magnetic particles I, followed by incubation for 20 min at room temperature with shaking. The solid phase in these samples was separated using magnetic racks, washed twice with ECL buffer, resuspended in 530 µl of ECL buffer and then analyzed for electrochemiluminescence as described in Example 1. FIG. 3 illustrates this assay format. The results for this assay format were demonstrated with human papilloma virus samples (2,14). Specificity studies of the direct incorporation of Ru(bpy)$_3^{2+}$-label-oligonucleotides into biotinylated PCR products made use of the closely related virus types HPV16 and HPV18. Assay for the presence of HPV 16 and 18 using DNA samples positive for both virus types and oligonucleotides specific for each virus type. The primers were as follows 2PV16, 2PV18 were biotinylated and 3PV16, 3PV18 were Ru(bpy)$_3^{2+}$-label-oligonucleotides. The 2/3PV16 and 2/3PV18 oligonucleotides were specific for HPV 16 and 18 respectively. The resultant bead-captured Ru(bpy)$_3^{2+}$-label was analyzed for ECL as described in Example 1. The results were plotted as ECL counts for each sample primer combination see FIG. 6.

To demonstrated the quantitative nature of our assay format a standard curve of directly incorporated Ru(bpy)$_3^{2+}$-label and biotinylated oligonucleotides into HPV16 PCR products was generated. The resultant bead-bound Ru(bpy)$_3^{2+}$-label was analyzed for ECL as described in Example 1. The ECL peak photon counts were plotted verses increasing concentrations HPV 16 DNA, expressed as a ratio viral copies to total cellular DNA copies. The primers used in this analysis HPV16 were 1PV16 (biotin label) and 2PV16 Ru(bpy)$_3^{2+}$-label). DNA used for each PCR was maintained at a constant 1 µg using calf thymus DNA. The results for this standard curve are shown in FIG. 5. These results of specificity and quantitation for this format demonstrates the ability of these ECL labels to produce simple and rapid DNA based assays. It also demonstrates the ability of the label to interface readily in enzyme reactions without interfering in the enzymatic process.

Example 29

DNA-Probe Assay Format II. Detection and Determination of Point Mutations in the Human Ha-ras Oncogene PCR Amplified Product We carried out the PCR reactions of Ha-ras genes using oligos HRP1 and HRP2. Using biotinylated HRP1 with unlabeled HRP2 the resulting PCR product can hybridize to Ru(bpy)$_3^{2+}$-label probes, 2CHR and 2T24. Conversely using biotinylated HRP2 with unlabeled HRP1 the resulting PCR product can hybridize to Ru(bpy)$_3^{2+}$-label probes, 1CHR and 1T24. The DNA used was human placental (normal) and mouse NIH3T3 cell DNA, transfected with the mutant Ha-ras gene from the bladder carcinoma T24 (15).

The assay protocol was as follows; 90 µl of PCR reaction mixture was added to 600 µg of streptavidin coupled magnetic particles I, followed by incubation at room temperature for 30 min. The solid phase in these samples was separated using magnetic racks, washed with 50 mM NaOH, washed with hybridization buffer (0.9 M NaCl, 50 mM NaPO4, pH 7.7, 5 mM EDTA, 0.1% w/v ficoll, 0.1% w/v polyvinylpyrrolidone, 0.1% w/v bovine serum albumin) and resuspended in hybridization buffer containing 10 g/mL of the $Ru(bpy)_3^{2+}$-label-oligonucleotide. These samples were hybridized for 15 min at 66° C.

The solid phase was separated using magnetic racks, washed twice with 0.9M NaCl, 50 mM NaPO4, pH 7.7, 5 mM EDTA, washed with 3M tetramethylammonium chloride, 50 mM Tris-HCl, pH 8.0, 2 mM EDTA, 0.025% triton X-100 at room temperature once and at 66° C. twice for 20 min each. The solid phase was washed with ECL buffer three times, resuspended in 530 µl ECL buffer and electrochemiluminescence detected as described in Example 1. FIG. 4 illustrates this assay format.

The assays for Ha-ras PCR products using $P^{32}$ labeled probes were similar to those using $Ru(bpy)_3^{2+}$-label except the solid phase was finally resuspended in 250 µl of ECL buffer. These suspended samples were then transferred to 5 mL of scintillation fluid and counted on a Beckman LS-100C liquid scintillation counter.

In FIG. 8 we show data from a point mutation assay for the Ha-ras oncogene. The PCR was performed as illustrated in FIG. 4 using biotinylated HRP2 with unlabeled HRP1 (for probes 1T24 and 1CHR) and biotinylated HRP1 with unlabeled HRP2 (for probes 2T24 and 2CHR), generating bead-bound single stranded targets for hybridization. The DNA samples were the normal (Placenta) Ha-ras Gene and the mutant (NIH3T3-T24) Ha-ras Gene. The hybridization of the bead-bound DNA with $Ru(bpy)_3^{2+}$-label-1T24 (1T24), $Ru(bpy)_3^{2+}$-label-2T24 (2T24), $Ru(bpy)_3^{2+}$-label-1CHR (1CHR) and $Ru(bpy)_3^{2+}$-label-2CHR (2CHR) was followed by TEMAC washes. Resultant bead-bound $Ru(bpy)_3^{2+}$-label was analyzed for ECL as described in Example 1. Results were plotted as ECL counts for each sample probe combination. The results (FIG. 8) were as expected with the normal probes hybridizing well to the normal DNA (see the CHR probes) and the mutant probes hybridizing to the mutant gene (see the T24 probes). It was of interest that these probes did not all perform equivalently. To investigate this apparent anomaly we studied these probes further using $P^{32}$ labeled probes with and without $Ru(bpy)_3^{2+}$-label. This Evaluation of the specificity of the $Ru(bpy)_3^{2+}$-label probes using $P^{32}$ labeled probes for the Ha-ras oncogene was carried out as follows. The PCR was performed as described in FIG. 8 using only biotinylated HRP2 with unlabeled HRP1 (for probes 1T24 and 1CHR). The probes used were: 1T24 and 1CHR containing $P^{32}$ (1T24-P, 1CHR—P) as controls. With the 1T24 and 1CHR containing both $P^{32}$ and $Ru(bpy)_3^{2+}$-label to determine the effects of the $Ru(bpy)_3^{2+}$-label. The samples were washed as earlier with TEMAC. The resultant bead-bound $P^{32}$ was analyzed on addition of scintillation cocktail in a scintillation counter. The results were plotted as $P^{32}$ counts per second for each sample probe combination (see FIG. 9). This result demonstrated that the $P^{32}$ probes and the $Ru(bpy)_3^{2+}$-labeled probes function equivalently and that problems with the probe specificity are due to the specific probe sequences used. To further demonstrate this equivalence of our $Ru(bpy)_3^{2+}$-label and $P^{32}$ we conducted an comparison between these labeled probes. The amplification was performed as previously described using placental DNA, using biotinylated HRP2 with unlabeled HRP1 (for probes 1T24 and 1CHR). The resultant PCR product was then sampled to give a set of samples containing differing amounts of product. These sets of samples were then hybridized with either probes labeled with $P^{32}$ (1T24-P32 and 1CHR-P32) or $Ru(bpy)_3^{2+}$-label (1T24-$Ru(bpy)_3^{2+}$ and 1CHR—$Ru(bpy)_3^{2+}$). The results from each study were then normalized using the average value from each label for the 90 µl of sample. These normalized figures allow a more effective comparison of signal to background and the comparative response of the two methods. The inset to FIG. 10 illustrates the response at the lower level of the dilution curve. The samples were handled as described earlier (FIG. 8 and FIG. 9). Results in FIG. 10 demonstrated the equivalency of the two labels with indications of a better response from our $Ru(bpy)_3^{2+}$-labeled probe. These studies demonstrated the ability of $Ru(bpy)_3^{2+}$-labeled probes to function as well as $P^{32}$ labeled probes in their ability to discriminate single base changes in sample DNA. This evidence indicates that the $Ru(bpy)_3^{2+}$-label does little to affect the properties of the labeled probe in hybridization reactions.

Example 30

DNA-Probe Assay Format III. Detection and Quantitation of Human Papilloma Virus PCR Products in a Non-Separation Assay For the non-separation assay on HPV 18, we performed an asymmetric PCR reaction with an excess of the biotinylated primer. This PCR reaction generates an excess of biotinylated single-stranded DNAs now available for direct hybridization by the $Ru(bpy)_3^{2+}$-label-probes.

For hybridization, we added 1000 ECL counts of $Ru(bpy)_3^{2+}$-label-oligonucleotide (~2 ng) specific for the HPV gene amplified to 15 µl of the PCR after completion of the amplification followed by incubation for 15 min at 50° C. To this hybridization mixture we added 60 µl of ECL buffer containing 600 µg of streptavidin coupled magnetic particles I and incubated with shaking at room temperature for 15 min. The sample volume was increased to 530 µl by addition of ECL buffer followed by detection of electrochemiluminescence as described in Example 1. FIG. 5 illustrates this assay format. To demonstrate this non-separation assay we ran a standard curve of HPV18 DNA. The PCR was performed using biotinylated 2PV18 and unlabeled 1PV18 using HeLa DNA (14). The resultant PCR reaction was then hybridized with the specific probe $Ru(bpy)_3^{2+}$-label-3PV18. The hybridization mixture was then added to streptavidin coated particles and the resultant bead-bound $Ru(bpy)_3^{2+}$-label was directly analyzed for ECL as described in Example 1. The results were plotted as ECL counts verses HPV18 copies added to the PCR with a control of the ras oligonucleotide probe (see FIG. 11). These results demonstrate the ability to generate rapid non-separation assays for nucleic acid sequences based on the properties of the ECL assay system.

Example 31

Assay for Specific Genomic DNA Sequences

The assay format described here makes use of two oligonucleotides, both hybridize to the same DNA strand next to each other, one probe allows capture; the other labels the complex (sandwich hybridization). This assay was demonstrated using *E. coli* DNA and probes specific for the trp E/D gene region. The *E. coli* DNA was prepared following standard protocols (16). The salmon sperm control DNA was purchased from Sigma Ltd. To the samples of DNA were added 14 µl of hybridization buffer (10× PBS, 10 mMEDTA and 0.7% SDS), 2 ng of biotin labeled TRP.CO4 and 5 ng of $Ru(bpy)_3^{2+}$-label TRP.CO3. These samples were made up to 100 µl with water. The samples were heated to 97° C. and incubated at 97° C. for 10 min, cooled to 50° C. and hybridized for 2 hrs. To these samples we added 20 μl of streptavidin coated magnetic particles II and mixed for 2 hrs at room temperature. The particles were then washed 4 times in ECL buffer resuspended in 500 μl of ECL buffer and analyzed as described in Example 3. The positive DNA is *E. coli* and the negative DNA is salmon sperm. The results are shown in Table X.

TABLE X

| DNA | Amount | Average ECL counts |
| --- | --- | --- |
| Positive | 10 | 184 |
|  | 25 | 257 |
|  | 50 | 266.5 |
| Negative | 10 | 87 |
|  | 25 | 70 |
|  | 50 | 75 |

These results demonstrated the ability of the ECL assay system to function in the detection of a genomic gene in *E. coli* using a sandwich hybridization assay format on non amplified DNA.

Example 32

Particle Concentration on Evanescent-Wave Fluorescence Detectors

Figure 22:
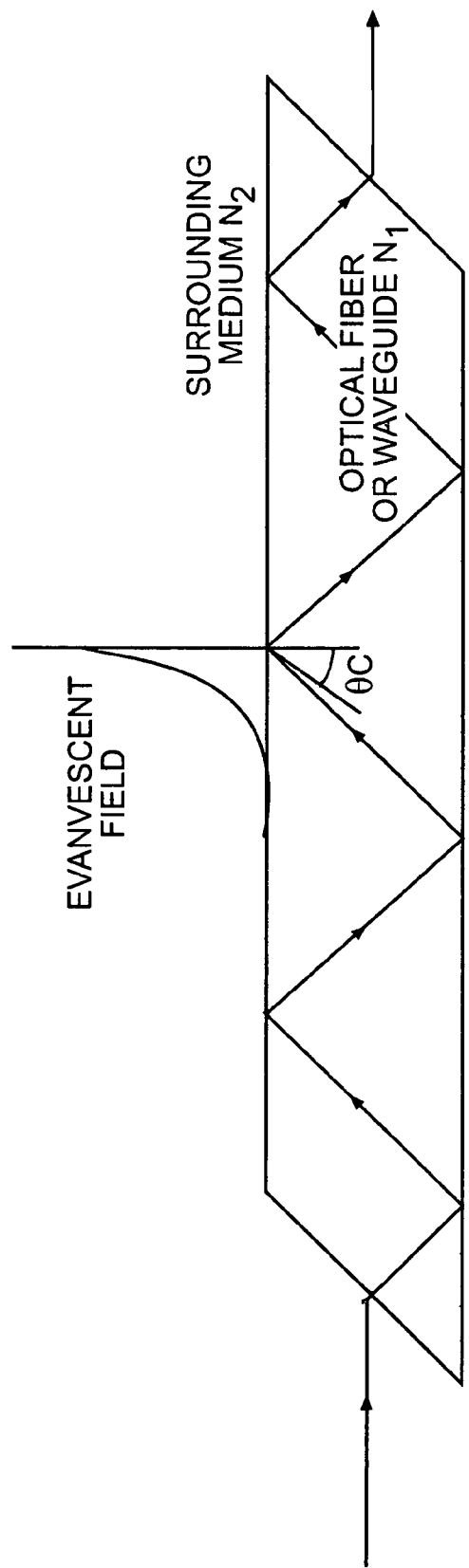
FIG. 22 is a schematic representation of an evanescent-wave fluorescence detection.

Concentration of labeled complex on a detection surface can be used to increase sensitivity of assays using evanescent wave detectors. Such detectors may use either optical fibers or planar optical waveguides to carry light from a light source to the fluid environment. The light is reflected through the waveguide or optical fiber by total internal reflection (TIR) which occurs when an incident light beam strikes an interface between a dielectric medium of high refractive index ($n_1$) and one of lower refractive index ($n_2$). When the incident angle of the light beam is greater than the critical angle, $\theta_0 = \sin^{-1}(n_2/n_1)$, then the light is 100% internally reflected at the interface. In optical waveguides and optical fibers, light travels with an incidence angle greater than this critical angle, and propagates through the medium by total internal reflectance. FIG. 22 depicts the TIR propagation in a waveguide or optical fiber.

Although the light ray is totally reflected at each interaction with the interface, the electromagnetic field is not zero outside the medium. Physical requirements of continuity across an interface require that the electromagnetic field decay exponentially as it penetrates outside the fiber or waveguide into the external environment. This field is called the evanescent field and is capable of exciting fluorophores to fluoresce. The decay rate of the evanescent field depends on the incident wavelength, refractive indices $n_1$ and $n_2$, and the angle of incidence. Using a quartz waveguide and visible light in a water environment, the evanescent field decays by approximately 90% within a distance of 100 nm from the waveguide/solution interface.

The same principles which create the evanescent field for light propagating in the waveguide or optical fiber allow the light which is generated when fluorophores luminesce to be captured back into the optical element efficiently. Additionally, any light produced outside the evanescent zone is efficiently rejected from entering the optical element. The combination of these effects allows optical fibers or waveguides to be used as efficient optical elements for measuring the presence of and concentration of fluorophore labels on or near their surfaces in an aqueous environment. U.S. Pat. No. 4,447,546 describes one suitable method and apparatus for conducting fluorescence immunoassays employing an optical fiber to excite and measure evanescent zone fluorescence from labelled immunoreactant.

The invention can be applied to improve the sensitivity of fluorescent binding assays using optical fibers or waveguides. The assay is performed using reagents labelled with fluorescent moieties. After incubation of the particles, sample and reagents, the particles are concentrated upon the surface of the waveguide or optical fiber. Because the surface area of the particles is greater than the geometric area of the waveguide or optical fiber, more fluorophores can be collected in the evanescent zone surrounding the optical element. Hence, the luminescent signal from the particles will be larger and quantitation of analyte will be more sensitive, resulting in improved detection limits.

What is claimed is:

1. An apparatus for performing a binding assay for an analyte of interest in a sample based upon measurement of electrochemiluminescence at an electrode surface comprising:
   (a) a flow-through cell defining a sample containing volume intersecting with an inlet and an outlet;
   (b) a pump located upstream or downstream of said flow-through cell for drawing a sample into said cell;
   (c) an electrode having an electrode surface exposed to and positioned adjacent a portion of the sample containing volume;
   (d) a voltage control device for impressing electrochemical energy upon said electrode sufficient to generate luminescence;
   (e) means for magnetically collecting particles along said electrode surface; and
   (f) a light detection device for measuring the luminescence generated at said electrode.

2. The apparatus as defined in claim 1, wherein said collecting means comprises a magnet that exerts a magnetic field in a zone proximate said electrode surface.

3. The apparatus as defined in claim 2, wherein said magnet is located below said electrode.

4. The apparatus as defined in claim 3, wherein said magnet is capable of being removed from the magnet's location beneath said electrode during the operation of said light detection device.

5. The apparatus as defined in claim 2, wherein said magnet comprises either a permanent magnet or an electromagnet.

6. The apparatus as defined in claim 2, wherein said magnet is a permanent magnet.

7. The apparatus as defined in claim 2, wherein said magnet is an electromagnet.

8. An apparatus for performing a binding assay for an analyte of interest in a sample based upon measurement of electrochemiluminescence at an electrode surface comprising:

(a) a flow-through cell defining a sample containing volume intersecting with an inlet and an outlet;
(b) a pump located upstream or downstream of said flow-through cell for drawing a sample into said cell;
(c) an electrode having an electrode surface exposed to and positioned adjacent a portion of the sample containing volume;
(d) a voltage control device for impressing electrochemical energy upon said electrode sufficient to generate luminescence;
(e) a magnetic particle collector along said electrode surface; and
(f) a light detector for measuring the luminescence generated at said electrode.

9. The apparatus as defined in claim 8, wherein said collector comprises a magnet that exerts a magnetic field in a zone proximate said electrode surface.

10. The apparatus as defined in claim 9, wherein said magnet is located below said electrode.

11. The apparatus as defined in claim 10, wherein said magnet is capable of being removed from the magnet's location beneath said electrode during the operation of said light detector.

12. The apparatus as defined in claim 9, wherein said magnet comprises either a permanent magnet or an electromagnet.

13. The apparatus as defined in claim 9, wherein said magnet is a permanent magnet.

14. The apparatus as defined in claim 9, wherein said magnet is an electromagnet.

* * * * *

UNITED STATES PATENT AND TRADEMARK OFFICE
CERTIFICATE OF CORRECTION

| | | |
|---|---|---|
| PATENT NO. | : 7,462,322 B2 | Page 1 of 1 |
| APPLICATION NO. | : 10/912574 | |
| DATED | : December 9, 2008 | |
| INVENTOR(S) | : Leland et al. | |

It is certified that error appears in the above-identified patent and that said Letters Patent is hereby corrected as shown below:

On the Title page,

[*] Notice:   Subject to any disclaimer, the term of this patent is extended or adjusted under 35 USC 154(b) by 508 days Delete the phrase "by 508 days" and insert -- by 836 days --

Signed and Sealed this

Eighteenth Day of May, 2010

David J. Kappos
*Director of the United States Patent and Trademark Office*